(12) United States Patent
Barrera et al.

(10) Patent No.: US 9,580,670 B2
(45) Date of Patent: *Feb. 28, 2017

(54) CONSUMER PRODUCT COMPOSITIONS COMPRISING ORGANOPOLYSILOXANE CONDITIONING POLYMERS

(71) Applicant: The Procter & Gamble Company, Cincinnati, OH (US)

(72) Inventors: Carola Barrera, West Chester, OH (US); Steven Daryl Smith, Fairfield, OH (US); Robert Joseph McChain, Cincinnati, OH (US); Yonas Gizaw, West Chester, OH (US); Rajan Keshav Panandiker, West Chester, OH (US); Michael Albert Snyder, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/604,781

(22) Filed: Jan. 26, 2015

(65) Prior Publication Data

US 2015/0147286 A1 May 28, 2015

Related U.S. Application Data

(63) Continuation of application No. PCT/US2013/052592, filed on Jul. 29, 2013.

(51) Int. Cl.
| | | |
|---|---|---|
| *C08G 77/26* | (2006.01) | |
| *C11D 3/16* | (2006.01) | |
| *A61K 8/898* | (2006.01) | |
| *A61Q 5/12* | (2006.01) | |
| *A61Q 5/02* | (2006.01) | |
| *C11D 3/37* | (2006.01) | |

(52) U.S. Cl.
CPC ............. *C11D 3/162* (2013.01); *A61K 8/898* (2013.01); *A61Q 5/02* (2013.01); *A61Q 5/12* (2013.01); *C11D 3/3742* (2013.01); *C08G 77/26* (2013.01)

(58) Field of Classification Search
CPC ..................................................... C08G 77/26
See application file for complete search history.

(56) References Cited

U.S. PATENT DOCUMENTS

| | | | |
|---|---|---|---|
| 3,560,543 A | 2/1971 | Plueddemann | |
| 4,200,724 A | 4/1980 | Darms et al. | |
| 4,293,397 A | 10/1981 | Sato | |
| 4,533,714 A | 8/1985 | Sebag et al. | |
| 4,833,225 A * | 5/1989 | Schaefer ................ | A61K 8/898 424/70.122 |
| 5,300,167 A | 4/1994 | Nohr et al. | |
| 5,358,667 A | 10/1994 | Bergmann | |
| 5,476,660 A | 12/1995 | Somasundaran | |
| 5,659,001 A | 8/1997 | De La Croi Habimana et al. | |
| 5,925,341 A | 7/1999 | Cervantes et al. | |
| 6,093,240 A | 7/2000 | Matsumura et al. | |
| 6,201,058 B1 | 3/2001 | Mahr et al. | |
| 6,338,855 B1 | 1/2002 | Albacarys | |
| 6,395,858 B1 | 5/2002 | Mack et al. | |
| 6,491,838 B1 | 12/2002 | Standke et al. | |
| 6,641,870 B2 | 11/2003 | Bartkowiak et al. | |
| 6,833,344 B2 | 12/2004 | Boutique | |
| 6,878,770 B2 * | 4/2005 | Herzig .................... | C03C 17/30 106/287.11 |
| 6,903,061 B2 | 6/2005 | Masschelein | |
| 7,118,057 B2 | 10/2006 | Hao | |
| 7,217,777 B2 | 5/2007 | Lange et al. | |
| 7,294,612 B2 | 11/2007 | Popplewell et al. | |
| 7,514,091 B2 | 4/2009 | Restle et al. | |
| 7,563,856 B2 | 7/2009 | Lange | |
| 7,563,857 B2 | 7/2009 | Lange | |
| 7,871,972 B2 | 1/2011 | SenGupta | |
| 7,888,306 B2 | 2/2011 | SenGupta | |
| 8,158,572 B2 | 4/2012 | Schubert | |
| 8,367,791 B2 | 2/2013 | Byrd et al. | |
| 8,440,174 B2 | 5/2013 | Panandiker | |
| 2003/0147842 A1 | 8/2003 | Restle et al. | |
| 2004/0029981 A1 | 2/2004 | Herzig et al. | |
| 2004/0048996 A1 | 3/2004 | Lange | |
| 2004/0092424 A1 | 5/2004 | Boutique et al. | |
| 2004/0092425 A1 | 5/2004 | Boutique et al. | |
| 2004/0138400 A1 | 7/2004 | Lange | |
| 2005/0009721 A1 | 1/2005 | Delplancke et al. | |
| 2005/0170994 A1 | 8/2005 | Casado-Dominguez | |
| 2006/0235181 A1 | 10/2006 | Lange et al. | |
| 2007/0041929 A1 | 2/2007 | Torgerson | |
| 2007/0041930 A1 | 2/2007 | Meder et al. | |

(Continued)

FOREIGN PATENT DOCUMENTS

| | | |
|---|---|---|
| CN | 101956324 | 1/2011 |
| JP | Hei 07-053330 | 2/1995 |

(Continued)

OTHER PUBLICATIONS

JP 07-053330, Feb. 1995.*
JP 05-320349, Dec. 1993.*
English language translation JP 2002/308723, Oct. 2002.*
U.S. Appl. No. 14/604,776, filed Jan. 26, 2015, Steven Daryl Smith et al.
U.S. Appl. No. 14/604,778, filed Jan. 26, 2015, Steven Daryl Smith et al.
U.S. Appl. No. 14/604,779, filed Jan. 26, 2015, Yonas Gizaw et al.
U.S. Appl. No. 14/604,782, filed Jan. 26, 2015, Carola Barrera et al.
International Search Report and Written Opinion dated Oct. 15, 2013, 9 pgs.

(Continued)

*Primary Examiner* — Margaret Moore
(74) *Attorney, Agent, or Firm* — Jason J Camp

(57) ABSTRACT

Consumer product compositions comprising organopolysiloxane conditioning polymers. Also disclosed are processes for making such compositions and to methods of using such compositions to provide a conditioning benefit.

16 Claims, No Drawings

(56) References Cited

U.S. PATENT DOCUMENTS

| | | | |
|---|---|---|---|
| 2009/0142293 A1* | 6/2009 | Wagner | A61K 8/898 424/78.37 |
| 2010/0041583 A1 | 2/2010 | Ponder | |
| 2010/0215604 A1 | 8/2010 | Van Flodrop et al. | |
| 2010/0247472 A1 | 9/2010 | Sau | |
| 2011/0135588 A1 | 6/2011 | Uehara | |
| 2012/0037040 A1 | 2/2012 | Standke et al. | |
| 2012/0276175 A1 | 11/2012 | Dihora | |
| 2014/0020188 A1 | 1/2014 | Gizaw et al. | |
| 2014/0024780 A1 | 1/2014 | Benlahmar et al. | |
| 2014/0030206 A1 | 1/2014 | Smith et al. | |
| 2014/0128521 A1 | 5/2014 | Sekiya et al. | |
| 2014/0206805 A1 | 7/2014 | Sekiya et al. | |
| 2015/0225313 A1 | 8/2015 | Schmidt et al. | |
| 2015/0307417 A1 | 10/2015 | Schmidt et al. | |

FOREIGN PATENT DOCUMENTS

| | | | |
|---|---|---|---|
| JP | Hei 07-053331 | | 2/1995 |
| JP | Hei 07-053332 | | 2/1995 |
| JP | 2002/308723 | * | 10/2002 |
| JP | 2002-308723 | A | 10/2002 |
| JP | A-2002-308723 | | 10/2002 |
| JP | A-2002-308991 | | 10/2002 |
| JP | Hei 05-320349 | | 10/2013 |
| WO | WO9811870 | A1 | 3/1998 |
| WO | 99/32539 | * | 7/1999 |
| WO | WO9932539 | A1 | 7/1999 |
| WO | WO 00/71806 | | 11/2000 |
| WO | WO 02/18528 | | 3/2002 |
| WO | WO 2004/041987 | | 5/2004 |
| WO | WO 2005/009721 | A1 | 2/2005 |
| WO | WO 2011/123727 | A | 10/2011 |
| WO | WO 2014/018985 | | 1/2014 |

OTHER PUBLICATIONS

International Search Report and Written Opinion dated Oct. 30, 2013, 8 pgs.

International Search Report and Written Opinion dated Oct. 30, 2013, 9 pgs.

International Search Report and Written Opinion dated Oct. 18, 2013, 9 pgs.

* cited by examiner

CONSUMER PRODUCT COMPOSITIONS COMPRISING ORGANOPOLYSILOXANE CONDITIONING POLYMERS

FIELD OF INVENTION

The present application relates to consumer product compositions comprising organopolysiloxane conditioning polymers. It also relates to processes for making such compositions and to methods of using such compositions to deliver conditioning benefits onto substrates.

BACKGROUND OF THE INVENTION

Conditioning polymers meant for deposition onto negatively charged surfaces, such as fabric, skin, or hair, are included in many common consumer product compositions. Such products can provide consumer-desired benefits such as softness, lubricity, hand, anti-wrinkle, hair conditioning, frizz control, skin miniaturization, and color protection. Difficulties frequently arise in achieving effective conditioning agent deposition onto these surfaces, especially when the conditioning agent is delivered in the form of rinse-off compositions, such as hair shampoos, body washes, detergents, and fabric softeners, as well as other surface cleansing and surface treatment products.

Various quaternized aminosilicone polymers have been proposed for use as conditioning polymers. The effectiveness of any particular conditioning polymer depends not only upon the chemical and physical properties of the conditioning polymer itself, but also upon those of the targeted surface, as well as various other materials that may be included in the composition. Thus, a conditioning polymer delivering exemplary performance under one set of conditions may provide little or no advantage in another. In order to ensure desired performance, the conditioning polymer should possess properties that complement those of the particular targeted surface and consumer product formulation.

Varying structural parameters, such as molecular weight, cationic charge, hydrophobic substitution, and/or hydrophilic substitution, such as degree of ethoxylation, can significantly impact performance of cationic conditioning polymers. Adjusting these parameters provides a way to modify and control performance aspects of these polymers on a substrate. Further, in order to obtain optimal conditioning benefits, the silicone polymer must be functionalized to favorably interact with the particular substrate to which it will be applied. In addition, the silicone polymer must be able to be formulated into a stable composition that provides the desired level of shelf-stability.

The quaternized aminosilicone polymers must be formulated into consumer-acceptable products. Consumer products such as those in the areas of fabric care, beauty care, pet care, and home care, are most typically aqueous-based products. Aqueous product formulations can be facilitated, for example, by incorporating hydrophilic moieties such as ethoxylate, propoxylate, and more generally alkoxylate moieties into the polymer itself. Alternately, the hydrophobic polymers can be emulsified into the aqueous based products.

Unfortunately, incorporating benefit agents into aqueous based products, especially benefit agents which are hydrophobic and/or surfactant-soluble and/or hydrophilically modified, often results in the benefit agent being preferentially rinsed away from the intended site of deposition, rather than being deposited. The loss of the hydrophobic benefit agents can be particularly pronounced in dilute systems.

Without being bound by theory, the loss of hydrophobic benefit agents can result from the cationic charge being distributed too randomly along the length of the benefit agent polymer. In many cases, the charge is too highly dispersed to adequately facilitate surface deposition.

A further problem occurs in the formulation of quaternized aminosilicone polymers in the context of cleansing compositions (e.g., shampoos), a great number of which (e.g., shampoos, bar soap, and skin cleansing compositions) contain anionic surfactants. Deposition of anionic or non-ionic actives onto anionic surfaces from compositions containing anionic surfactants can be especially problematic. Various compositions comprising cationic polymers (e.g., quaternized amines) have been proposed as conditioning polymers in such compositions, however they may not be wholly satisfactory as commercial products.

Without being bound by theory, anionic surfactants can interfere with deposition of actives, including cationic actives, by adsorbing on all surfaces as well as forming complexes/precipitates with the cationic conditioning polymers before the actives can deposit on the targeted surface. Even if deposition occurs, the formulations may exhibit poor stability due to flocculation and precipitation. However, the higher the concentration of anionic surfactant, the more difficult it is to attain active deposition. Among other disadvantages, this leads to non-cost-effective use and waste of materials.

Several cationic conditioning polymer materials exist in the art, but are not wholly satisfactory. There is still a need to provide silicone polymers that are suitable for use in a wide range of consumer product applications. Applicant is not aware of any prior silicone polymer that meets all the desired versatility, shelf-stability, and performance criteria desired in a consumer product context.

For example, the quaternized aminosilicone polymer material described by Ono (WO 99/32539) comprises end groups having heteroatoms such as oxygen, nitrogen, or sulfur, or halogens. These functionalized end groups can lead to undesirable reactions that pose stability issues for compositions comprising these materials. For instance, Ono's silicones can react further through these end groups, leading to further condensation/polymerization of the silicones in the compositions during storage.

Also known in the art are quaternized silicones that include alkylene oxide units, such as U.S. Pat. No. 6,903,061 to Masschelein. The quaternized silicones described by Masschelein tend to be too water soluble, and thus have a reduced capacity as conditioning polymers, since these materials tend to partition into water at a higher than desired level. Further, these materials may have an undesirable feel because of their high permeability to water and water vapor. Further, because of their water solubility, these materials can be difficult to formulate reproducibly. Further, Masschelein discloses materials having only one quaternized nitrogenous group per side of the molecule. This can limit the desired degree of functionality in a silicone material. It would desirable to have a material the provides greater flexibility via the level of quaternization. Similarly, the ethoxylated quaternized silicone materials disclosed by Boutique in U.S. Pat. No. 6,833,344, suffer from many of the same inadequacies of those described by Masschelein.

Unfortunately, such care agents are incompatible with a variety of other consumer product ingredients, not stable over long-term storage, and/or do not deposit well-enough onto the target surface, necessitating their inclusion at levels higher than would otherwise be required if they deposited more efficiently.

Accordingly, it is an object of the present invention to provide consumer product compositions comprising conditioning polymers that can effectively deposit and provide conditioning benefits to substrates while avoiding the aforementioned disadvantages.

SUMMARY OF THE INVENTION

The present invention attempts to solve one or more of the aforementioned needs by providing, in one aspect, consumer product compositions comprising an inventive organopolysiloxane conditioning polymer. The invention also relates to methods of making such compositions and to methods of using such compositions to provide conditioning benefits to substrates treated therewith.

In one aspect, the present invention provides a cleansing or surface treatment consumer product composition comprising an adjunct and a blocky cationic organopolysiloxane having the formula:

$$M_w D_x T_y Q_z$$

wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$ or G$_3$; and G$_1$, G$_2$, and G$_3$ are each independently selected from the formula:

$$-X-N\overset{R_4(n)}{|}+E-N\overset{R_4(n)}{|}-E'-N\overset{R_4(n)}{|}\Big]_p-R_4 \quad kA^{-t}$$

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O. Alternatively, each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene;
N=a nitrogen atom;
R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;
E comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;
E' comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

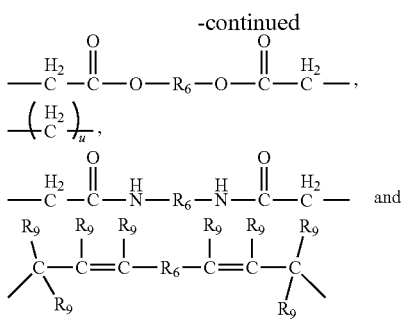

wherein:

$R_6$ comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E' radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;

n is an integer independently selected from 1 or 2;

when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; where t is an integer independently selected from 1, 2, or 3; and k≤(p*2/t)+1; such that the total number of cationic charges balances the total number of anionic charges in the organopolysiloxane molecule; and wherein at least one E does not comprise an ethylene moiety. $A^{-t}$ can be selected from the group consisting of Cl$^-$, Br$^-$, I$^-$, methylsulfate, toluene sulfonate, carboxylate, phosphate, hydroxide, acetate, formate, carbonate, nitrate, and combinations thereof; or alternatively from the group consisting of Cl$^-$, Br$^-$, I$^-$, methylsulfate, toluene sulfonate, carboxylate, phosphate and combinations thereof. The organopolysiloxane can have a charge density of from 0.04 meq/g to 12 meq/g, or from 0.04 meq/g to 4 meq/g; or from 1 meq/g to 12 meq/g. In some embodiments, w is an integer from 2 to 50, and in others w is equal to 2. In particular embodiments, x is an integer from 10 to 4,000, or from 40 to 2,000. In one embodiment, w is equal to 2, x is an integer from 20 to 1,000, and y and z are 0.

In one embodiment, $G_1$, $G_2$ and $G_3$ are identical; in another embodiment, $G_1$ and $G_2$ are the same while $G_3$ is different; and in another embodiment, each of $G_1$, $G_2$, and $G_3$ are different. For at least one of $G_1$, $G_2$ or $G_3$, m can be an integer independently selected from 2 to 50, or from 2 to 25, or from 2 to 10. Or, for at least one of $G_1$, $G_2$ or $G_3$, k can be an integer independently selected from 0 to 101, or from 2 to 50. In at least one embodiment, y=z=0. In some embodiments, from 50% to 100% of the amines present in the molecule can be quaternized, or from 70% to 100%, or from 90% to 100%.

One skilled in the art will recognize that the blocky organopolysiloxane of the present invention encompasses a plethora of different embodiments. To this end, when both y and z equal zero, the blocky organopolysiloxane of the present invention can be represented by the formula:

$$M_w D_x$$

where:
$M=[SiR_1R_2R_3O_{1/2}]$, $[SiR_1R_2G_1O_{1/2}]$, $[SiR_1G_1G_2O_{1/2}]$, $[SiG_1G_2G_3O_{1/2}]$, or combinations thereof;
$D=[SiR_1R_2O_{2/2}]$;
w=is an integer from 1 to 2;
x=is an integer from 5 to 15,000;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;
at least one of M or D incorporates at least one moiety $G_1$, $G_2$ or $G_3$, and $G_1$, $G_2$, and $G_3$ are each independently selected from:

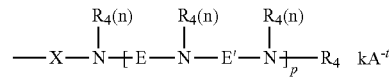

wherein:

X comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O. Alternatively, each X can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, and $C_6$-$C_{32}$ substituted arylalkylene;

N=a nitrogen atom;

$R_4$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;

E comprises a divalent radical selected from the group consisting of $C_1$-$C_{32}$ alkylene or $C_3$-$C_{32}$ alkylene, $C_1$-$C_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of $C_1$-$C_{32}$ alkylene or $C_3$-$C_{32}$ alkylene, $C_1$-$C_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

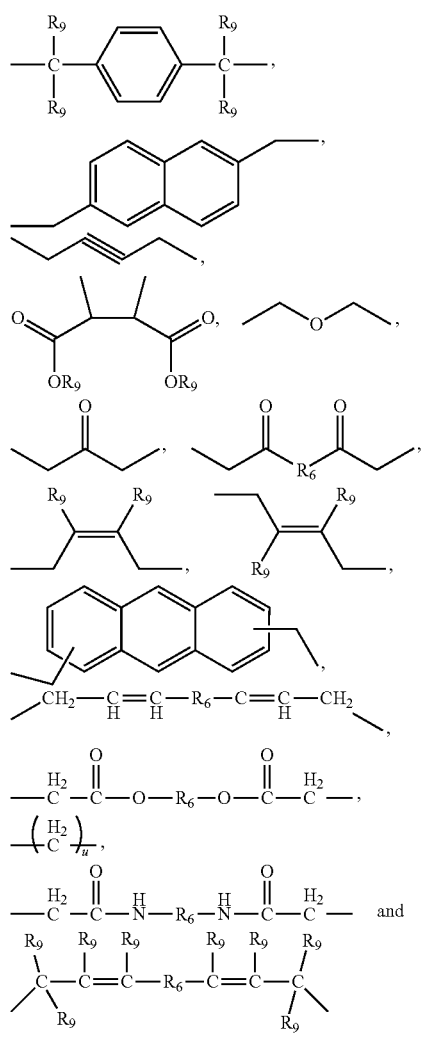

wherein:

$R_6$ comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E' radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;

n is an integer independently selected from 1 or 2;

when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; where t is an integer independently selected from 1, 2, or 3; and $k \le (p*2/t)+1$; such that the total number of cationic charges balances the total number of anionic charges in the organopolysiloxane molecule; and wherein at least one E does not comprise an ethylene moiety. $A^{-t}$ can be selected from the group consisting of $Cl^-$, $Br^-$, $I^-$, methylsulfate, toluene sulfonate, carboxylate, phosphate, hydroxide, acetate, formate, carbonate, nitrate, and combinations thereof; or alternatively from the group consisting of $Cl^-$, $Br^-$, $I^-$, methylsulfate, toluene sulfonate, carboxylate, phosphate and combinations thereof.

In one embodiment, E or E' is a primary alkyl chain having 3 or more carbon atoms, or 4 or more carbon atoms, or 5 or more carbon atoms, or from 4 to 32 carbon atoms. Without being limited by theory, it is believed that in embodiments where E or E' is a primary alkyl chain having exactly 2 carbon atoms, the moiety G can be unstable relative to the potential for an elimination reaction. This is because an undesirable elimination reaction is likely to take place, due to an unshared electron pair reacting to create an alkene.

In another embodiment, the moiety E or E' can be independently selected from different groups of different length to control the spacing and density of the charges along the chain. In certain applications, it can be desirable to have these charges closely spaced, and in other applications it can be desirable to have these charges spaced farther apart. The charged moiety G can be separate from the silicone portion of the organopolysiloxane, and more specifically, disposed at the terminal ends of the siloxane moiety. Without being bound by theory, it is believed that maintaining the charges in a "blocky" fashion disposed at the ends of a terminal siloxane moiety, allows the siloxane moiety to project further out from the surface of the treated substrate, resulting in a more lubricious, softer feel for the treated substrate.

Charged organopolysiloxanes can also be difficult to formulate, particularly into aqueous products, where they generally need to be emulsified. The use of longer spacers enables a less concentrated, more dispersed charge density into the aqueous medium of aqueous compositions comprising the organopolysiloxanes. This can result in better dispersion of the organopolysiloxanes during formulation. In one embodiment, X is a hydrocarbon moiety not comprising any heteroatoms (e.g., substantially free from any heteroatoms). Although not wishing to be limited by theory, the presence of reactive end groups is believed to result in unstable products that are not shelf-stable, due to their tendency to degrade or react with other materials in the composition over time or to be negatively impacted by destabilizing factors in the use environment.

In one embodiment, the terminal moieties of the organopolysiloxane are hydrocarbon groups not comprising any heteroatoms (e.g., substantially free from any heteroatoms). Without being bound by theory, it is believed that alkyl end groups of the organopolysiloxanes of the present invention are not as highly degradative or reactive, thus resulting in compositions that are more stable and have a suitably longer shelf-life.

The organopolysiloxane can have a charge density of from 0.05 meq/g to 12 meq/g; or from 0.1 meq/g to 10 meq/g; or from 0.1 to 5 meq/g. Further, the molecular weight of said organopolysiloxane can be from about 10,000 Daltons to about 1,000,000 Daltons; from about 20,000 Daltons to about 500,000 Daltons; or from about 25,000 Daltons to about 50,000 Daltons In one aspect, the consumer product composition can be selected from the group consisting of hair care compositions, fabric care compositions, skin care compositions, shampoos, hair conditioners, bodywashes, hair mousses, gels, pomades, sprays, laundry detergent, fabric softener, antimicrobial wash, hard surface cleaners, and carpet cleaners.

In one embodiment, the adjunct is selected from the group consisting of bleach, bleach activators, surfactants, builders, chelating agents, dye transfer inhibiting agents, dispersants, enzymes, enzyme stabilizers, catalytic metal complexes, polymers, polymeric dispersing agents, clay and soil removal/anti-redeposition agents, brighteners, fluorescent whitening agents, suds suppressors, dyes, perfumes, perfume delivery systems, structure elasticizing agents, fabric softeners, carriers, hydrotropes, solvents, processing aids, conditioning agents, perfume microcapsules, emollients, fatty alcohols, delivery enhancing agents, pigments, high melting point fatty compounds, cationic polymers, anti-dandruff actives, humectant, skin care actives, silicone, silicone resin, silicone waxes, a material comprising a hydrocarbon wax, a hydrocarbon liquid, a sugar polyester, a sugar polyether, hydrocarbon waxes, polyolefin waxes, polyethylene and polypropylene waxes, modified polyethylene and polypropylene waxes, polyisobutene, substituted polyisobutene, isobutene, essential oils, lipids, skin coolants, vitamins, sunscreens, antioxidants, glycerine, catalysts, silicon dioxide particles, malodor reducing agents, odor-controlling materials, antistatic agents, softening agents, insect and moth repelling agents, colorants, antioxidants, bodying agents, drape and form control agents, smoothness agents, wrinkle control agents, sanitization agents, antibacterial disinfecting agent, germ control agents, mold and mildew control agents, antiviral agents, drying agents, stain resistance agents, soil release agents, fabric refreshing agents and freshness extending agents, dye fixatives, dye transfer inhibitors, color maintenance agents, optical brighteners, color restoration/rejuvenation agents, anti-fading agents, whiteness enhancers, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, natural agents, antiperspirant actives, dyes, emollients, fatty alcohols, gel networks, and mixtures thereof.

In a particular embodiment, the adjunct comprises a material selected from the group consisting of a silicone, a silicone resin, a silicone wax, or combinations thereof.

The adjunct can comprise a surfactant selected from the group consisting of linear or branched alkyl benzene sulfonate, alkyl sulfate, alkyl ethoxy sulfate, alkyl ethoxylate, alkyl glyceryl sulfonate, quaternary ammonium surfactant, ester quaternary ammonium compound, and mixtures thereof.

In one embodiment, the adjunct comprises a material selected from the group consisting of:

a) an anionic surfactant selected from the group consisting of a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, alkyls, alkyl ether sulfates, succinnates, olefin sulfonates, beta-alkyloxy alkane sulfonates and mixtures thereof, b) a cationic surfactant selected from the group consisting of mono-long alkyl quaternized ammonium salt cationic surfactants, mono-alkyl amines, di-alkyl chain cationic surfactants, and mixtures thereof, c) a conditioning active selected from the group consisting of silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein, d) a high melting point fatty compound selected from the group consisting of fatty alcohols, fatty acids, fatty alcohol derivatives, fatty acid derivatives, and mixtures thereof, e) and mixtures thereof.

The adjunct can also comprise a surfactant, such as those selected from the group consisting of anionic, cationic, nonionic, zwitterionic, amphoteric, and combinations thereof. In some embodiments, the ratio of anionic surfactant to the sum of cationic and nonionic surfactants is from 10:1 to 1:10; or from 6:1 to 1:9; or from 5:1 to 1:8. Many fabric care compositions have adjuncts that comprise a cationic surfactant and a fabric softening active compound and/or a deposition aid.

The adjunct may comprise in one embodiment a material selected from the group consisting of cationic surfactants, high melting point fatty compounds, cationic polymers, conditioning agents, anti-dandruff actives, humectant, suspending agents, skin care actives, color cosmetics, and mixtures thereof. In other embodiments, the adjunct comprises a surfactant selected from the group consisting of alkyls, alkyl ether sulfates, succinnates, olefin sulfonates, beta-alkyloxy alkane sulfonates, and mixtures thereof. The adjunct can also comprise a high melting point fatty compound selected from the group consisting of fatty alcohols, fatty acids, fatty alcohol derivatives, fatty acid derivatives, and mixtures thereof. Other adjuncts can include those cationic surfactants selected from the group consisting of mono-long alkyl quaternized ammonium salt cationic surfactants, mono-alkyl amines, di-alkyl chain cationic surfactants, and mixtures thereof.

The consumer products can be in any suitable product form, such as rinse-off or leave-on compositions, as appropriate. The compositions can be cleansing or non-cleansing treatment compositions. Many adjuncts comprise a carrier for the consumer product compositions. The present invention also provides a method of treating a substrate, comprising contacting the substrate with the organopolysiloxane composition, such as in the form of a consumer product.

DETAILED DESCRIPTION OF THE INVENTION

Features and benefits of the various embodiments of the present invention will become apparent from the following description, which includes examples of specific embodiments intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.
I. Definitions As used herein "consumer product" means baby care, personal care, fabric & home care, family care (e.g., facial tissues, paper towels), feminine care, health care, beauty care and like products generally intended to be used or consumed in the form in which they are sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleansing and/or treatment composition" is a subset of consumer products that includes, unless otherwise indicated, personal care, fabric care, and home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening. The care agents can advantageously be used in household polishes and cleaners for floors and countertops to provide benefits such as enhanced shine. Care agents in fabric softeners can help preserve "newness" because of their softening properties, and those having elasticity can help smooth out wrinkles. The care agents can also enhance shoe cleaning and polishing products.

As used herein, the term "personal care cleansing and/or treatment composition" is a subset of cleaning and treatment compositions that includes, unless otherwise indicated, products for treating hair, including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products; liquid cleaning and disinfecting agents including antibacterial hand-wash types, cleaning bars, mouthwashes, denture cleaners, and dentifrice cleaners; hair shampoos and hair-rinses; shower gels, fine fragrances, and foam baths; substrate-laden products such as dry and wetted wipes and pads, nonwoven substrates, and sponges; as well as sprays and mists all for consumer or/and institutional use; and/or methods relating to oral care including toothpastes, tooth gels, tooth rinses, denture adhesives, and tooth whitening.

As used herein, the term "fabric and/or hard surface cleansing and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products, as applicable, may be in standard, concentrated or even highly concentrated form even to the extent that such products may in certain aspects be non-aqueous.

As used herein, articles such as "a" and "an" are understood to mean one or more of what is claimed or described.

As used herein, the terms "include", "contain", and "have" are non-limiting and do not exclude other components or features beyond those expressly identified in the description or claims.

As used herein, the terms "treatment agent", "benefit agent", "active", "active agent", and/or "care agent" and the like are used interchangeably to mean materials that can impart desirable aesthetic and/or functional properties (e.g., conditioning benefits such as softening or freshening) to a substrate.

As used herein, the terms "conditioning agent" and "conditioning aid" are used interchangeably to refer to a material that delivers desirable conditioning effects (e.g., benefits such as softening or freshening) to a substrate. Conditioning agents are a type of treatment agent.

As used herein, the term "conditioning polymer" means a polymer that delivers desirable conditioning effects (e.g., softening or freshening) to a substrate.

As used herein, the term "substrate" is synonymous and used interchangeably with the terms "situs" and "surface".

Unless otherwise indicated, all molecular weights are weight average molecular weights as determined by size exclusion chromatography using a MALS detector (SEC-MALS), as is commonly known by those skilled in the art. A MALS detector (Multi-Angle Light Scattering Detector, such as those manufactured by Malvern Instruments Ltd., Malvern, UK) determines absolute molecular weight, rather than relative molecular weight (i.e., determined relative to a standard).

Unless otherwise noted, all component (i.e., ingredient) or composition levels are in reference to the active portion of that component or composition, and are exclusive of impurities, for example, residual solvents or by-products, which may be present in commercially available sources of such components or compositions.

The term "charge density", as used herein, refers to the ratio of the number of positive charges on a monomeric unit of which a polymer is comprised, to the molecular weight of said monomeric unit. The charge density multiplied by the polymer molecular weight determines the number of positively charged sites on a given polymer chain. Charge density can also be expressed in the form of an equation as:

$$\text{charge density} = \frac{(\text{moles of Nitrogen})(\text{charge per Nitrogen})}{(\text{moles of polymer})(\text{molecular weight of the polymer})} \times 100$$

Non-limiting examples of substrates include paper products, fabrics, garments, hard surfaces, hair, and skin.

As used herein, "targeted substrate" means a substrate, or the relevant portion of a substrate, upon which deposition is intended.

As used herein, a "deposition aid" is a material that assists another material (e.g., a benefit agent) to deposit (e.g., adhere) to a targeted substrate. The term "deposition aid" is broad enough to encompass both polymeric deposition aids (i.e. "deposition polymer") and non-polymeric deposition aids.

As used herein, "adjunct" means an optional material that can be added to a composition to complement the aesthetic and/or functional properties of the composition.

As used herein, "auxiliary composition" refers to one or more compositions that when combined with a benefit agent emulsion of the present invention, form a consumer product composition. The auxiliary composition may be in the form of one or more ingredients or ingredient combinations.

As used herein, "carrier" means an optional material, including but not limited to a solid or fluid, that can be combined with a benefit agent (e.g., conditioning polymers) to facilitate delivery and/or use of the benefit agent.

As used herein, the term "solid" includes granular, powder, bar and tablet product forms.

As used herein, the term "fluid" includes liquid, gel, paste and gas product forms including unitized-dose forms that generally include a fluid composition enclosed in a pouch or other delivery vehicle.

As used herein, the term "particle" includes solid and semi-solid particles, as well as emulsion droplets.

Unless otherwise indicated, all percentages and ratios herein are by weight.

All percentages and ratios are calculated based on weight of the total composition unless otherwise indicated.

Unless specified otherwise, all molecular weights are given in Daltons.

As used herein, the term "hydrocarbon polymer radical" means a polymeric radical comprising only carbon and hydrogen.

As used herein, "ethylene moiety" means a divalent $CH_2CH_2$ moiety.

As used herein, the term "siloxyl residue" means a polydialkylsiloxane moiety.

As used herein, the nomenclature $SiO_{n/2}$ represents the ratio of oxygen and silicon atoms. For example, $SiO_{1/2}$ means that, on average, one oxygen atom is shared between two silicon atoms. Likewise $SiO_{2/2}$ means that, on average, two oxygen atoms are shared between two silicon atoms and $SiO_{3/2}$ means that, on average, three oxygen atoms are shared between two silicon atoms.

As used herein, the terms "substantially no", "substantially free of", and/or "substantially free from" mean that the indicated material is at the very minimum not deliberately added to the composition to form part of it, or, preferably, is not present at analytically detectable levels. It is meant to include compositions whereby the indicated material is present only as an impurity in one of the other materials deliberately included.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

II. Organopolysiloxane Conditioning Polymer

The conditioning polymer of the present invention can deliver to substrates one or more conditioning benefits. The concentration of the conditioning agent in the composition should be sufficient to provide the desired conditioning benefits, as will be apparent to one of ordinary skill in the art. Such concentration can vary with the conditioning performance desired, the type and concentration of other components, and other like factors.

Among the various advantages of the inventive organopolysiloxane, the present invention provides the ability to independently optimize the charge density and the hydrophobicity (i.e., the PDMS block length) of the molecule. Unlike other organopolysiloxanes in the art, the charge density of the inventive organopolysiloxane can be modified without modifying the PDMS (i.e. polydimethyl siloxane) block length. Thus, the present invention can provide a longer PDMS block length, which increases the conditioning feel benefit, while also having a high charge density, which leads to a higher level of surface deposition and retention. In contrast, past attempts in the art of which the applicants are aware necessitate the break-down of PDMS into smaller units in order to distribute the charge across the polymer chain. This leads to shorter PDMS block length between charges, which leads to a reduced conditioning feel benefit. A more concentrated charge leads to stronger interaction between the conditioning polymer and the targeted surface, leading to better deposition and retention of the conditioner to the surface.

Although not wishing to be limited by theory, it is believed that the longer the length of contiguous PDMS blocks, the higher the conditioning benefit will be, compared to a polymer having the same total number of PDMS blocks but being more highly dispersed between the charges in the form of smaller blocks. It is theorized that the ability of Si—O moieties to rotate is responsible for the polymer's conditioning feel. Thus longer contiguous PDMS blocks will provide better conditioning because the level of Si—O rotation increases as the length of contiguous PDMS blocks is increased.

The present invention provides blocky cationic organopolysiloxane polymer of the formula:

$$M_w D_x T_y Q_z$$

wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$ or G$_3$; and G$_1$, G$_2$, and G$_3$ are each independently selected from the formula:

$$-X-N\overline{\phantom{x}}[E-N-E'-N\overline{\phantom{x}}]_p R_4 \; kA^{-t}$$
$$\phantom{-X-N}\;\;R_4(n)\;\;\;\;\;R_4(n)\;\;\;\;\;R_4(n)$$

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O. Alternatively, each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene;
N=a nitrogen atom;
R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;
E comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;
E' comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;
In one embodiment, there are no E moieties that are ethylene moieties. Each E and E' can be an identical or different radicals. In some embodiments, E and E' are different radicals.

In some embodiments, at least one E or E' is independently selected from the group consisting of:

wherein:

$R_6$ comprises a divalent radical selected from the group consisting of $C_1$-$C_{32}$ alkylene, $C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E' radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;

n is an integer independently selected from 1 or 2;

when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; where t is an integer independently selected from 1, 2, or 3; and k≤(p*2/t)+1; such that the total number of cationic charges balances the total number of anionic charges in the organopolysiloxane molecule; and wherein at least one E does not comprise an ethylene moiety. $A^{-t}$ can be selected from the group consisting of Cl$^-$, Br$^-$, I$^-$, methylsulfate, toluene sulfonate, carboxylate, phosphate, hydroxide, acetate, formate, carbonate, nitrate, and combinations thereof; or alternatively from the group consisting of Cl$^-$, Br$^-$, I$^-$, methylsulfate, toluene sulfonate, carboxylate, phosphate and combinations thereof.

The organopolysiloxane can have a charge density of from 0.04 meq/g to 12 meq/g, or from 0.04 meq/g to 4 meq/g; or from 1 meq/g to 12 meq/g. In some embodiments, w is an integer from 2 to 50, and in others w is equal to 2. In particular embodiments, x is an integer from 10 to 4,000, or from 40 to 2,000. In one embodiment, w is equal to 2, x is an integer from 20 to 1,000, and y and z are 0.

In one embodiment, $G_1$, $G_2$ and $G_3$ are identical; in another embodiment, $G_1$ and $G_2$ are the same while $G_3$ is different; and in another embodiment, each of $G_1$, $G_2$, and $G_3$ are different. For at least one of $G_1$, $G_2$ or $G_3$, m can be an integer independently selected from 2 to 50, or from 2 to 25, or from 2 to 10. Or, for at least one of $G_1$, $G_2$ or $G_3$, k can be an integer independently selected from 0 to 101, or from 2 to 50. In at least one embodiment, y=z=0. In some embodiments, from 50% to 100% of the amines present in the molecule can be quaternized, or from 70% to 100%, or from 90% to 100%.

One skilled in the art will recognize that the blocky organopolysiloxane of the present invention encompasses a plethora of different embodiments. To this end, when both y and z equal zero, the blocky organopolysiloxane of the present invention can be represented by the formula:

$$M_wD_x$$

where:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$];
w=is an integer from 1 to 2;
x=is an integer from 5 to 15,000;

$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;

at least one of M or D incorporates at least one moiety $G_1$, $G_2$ or $G_3$, and $G_1$, $G_2$, and $G_3$ are each independently selected from:

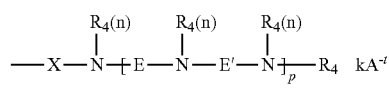

wherein:

X comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O. Alternatively, each X can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, and $C_6$-$C_{32}$ substituted arylalkylene;

N=a nitrogen atom;

$R_4$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;

E comprises a divalent radical selected from the group consisting of $C_1$-$C_{32}$ alkylene or $C_3$-$C_{32}$ alkylene, $C_1$-$C_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of $C_1$-$C_{32}$ alkylene or $C_3$-$C_{32}$ alkylene, $C_1$-$C_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

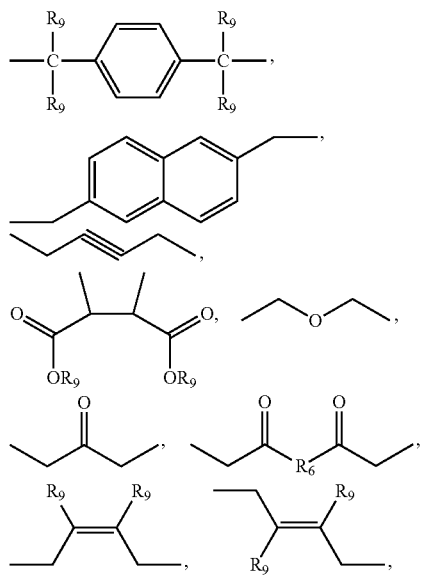

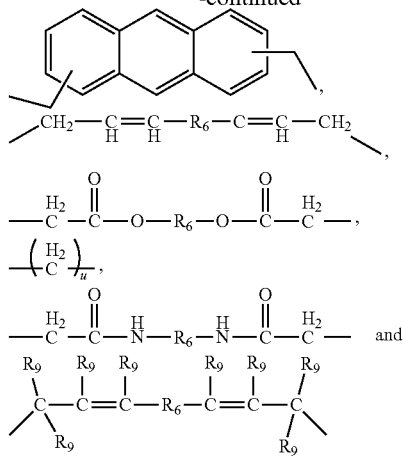

wherein:

$R_6$ comprises a divalent radical selected from the group consisting of $C_1$-$C_{32}$ alkylene, $C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E' radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;

n is an integer independently selected from 1 or 2;

when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; where t is an integer independently selected from 1, 2, or 3; and k≤(p*2/t)+1; such that the total number of cationic charges balances the total number of anionic charges in the organopolysiloxane molecule; and wherein at least one E does not comprise an ethylene moiety. $A^{-t}$ can be selected from the group consisting of Cl⁻, Br⁻, I⁻, methylsulfate, toluene sulfonate, carboxylate, phosphate, hydroxide, acetate, formate, carbonate, nitrate, and combinations thereof; or alternatively from the group consisting of Cl⁻, Br⁻, I⁻, methylsulfate, toluene sulfonate, carboxylate, phosphate and combinations thereof.

In one embodiment, E or E' is a primary alkyl chain having 3 or more carbon atoms, or 4 or more carbon atoms, or 5 or more carbon atoms, or from 4 to 32 carbon atoms. Without being limited by theory, it is believed that in embodiments where E or E' is a primary alkyl chain having exactly 2 carbon atoms, the moiety G can be unstable relative to the potential for an elimination reaction. This is because an undesirable elimination reaction is likely to take place, due to an unshared electron pair reacting to create an alkene.

In another embodiment, the moiety E or E' can be independently selected from different groups of different length to control the spacing and density of the charges along the chain. In certain applications, it can be desirable to have these charges closely spaced, and in other applications it can be desirable to have these charges spaced farther apart. The charged moiety G can be separate from the silicone portion of the organopolysiloxane, and more specifically, disposed at the terminal ends of the siloxane moiety. Without being bound by theory, it is believed that maintaining the charges in a "blocky" fashion disposed at the ends of a terminal siloxane moiety, allows the siloxane moiety to project further out from the surface of the treated substrate, resulting in a more lubricious, softer feel for the treated substrate.

Charged organopolysiloxanes can also be difficult to formulate, particularly into aqueous products, where they generally need to be emulsified. The use of longer spacers enables a less concentrated, more dispersed charge density into the aqueous medium of aqueous compositions comprising the organopolysiloxanes. This can result in better dispersion of the organopolysiloxanes during formulation. In one embodiment, X is a hydrocarbon moiety not comprising any heteroatoms (e.g., substantially free from any heteroatoms). Although not wishing to be limited by theory, the presence of reactive end groups is believed to result in unstable products that are not shelf-stable, due to their tendency to degrade or react with other materials in the composition over time or to be negatively impacted by destabilizing factors in the use environment.

In one embodiment, the terminal moieties of the organopolysiloxane are hydrocarbon groups not comprising any heteroatoms (e.g., substantially free from any heteroatoms). Without being bound by theory, it is believed that alkyl end groups of the organopolysiloxanes of the present invention are not as highly degradative or reactive, thus resulting in compositions that are more stable and have a suitably longer shelf-life.

The organopolysiloxane can have a charge density of from 0.05 meq/g to 12 meq/g; or from 0.1 meq/g to 10 meq/g; or from 0.1 to 5 meq/g. Further, the molecular weight of said organopolysiloxane can be from about 10,000 Daltons to about 1,000,000 Daltons; from about 20,000 Daltons to about 500,000 Daltons; or from about 25,000 Daltons to about 50,000 Daltons Further, in one embodiment, the organopolysiloxane of the present invention comprises multiple moieties E, which may be configured in an alternating pattern. The formula below depicts an instance of alternating moieties E and E', where E and E' are different (e.g., E=$C_2$ and E'=$C_{10}$).

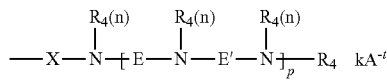

One of ordinary skill in the art would appreciate that the coefficient "p" would equal m/2. Without being bound by theory, it is believed that varying and/or alternating the various E moieties allows for additional control of charge density along the quaternary moiety. This enables targeted deposition of the organopolysiloxane. Thus, through the use of varied and alternating spacers, the present invention has the customization capability to provide specifically-tailored materials for the desired end use application and substrate.

Importantly, in accordance with the process disclosed herein for making the present organopolysiloxanes, the use of multiple differing and/or alternating E moieties can result in the particular multiple and/or alternating E moiety pattern desired. For example, one of the possible synthetic methods of making would lead to alternating E moieties. Said example would include incorporating the first said E moiety to a bis-halide compound and the second E moiety (i.e., E') into a bis-amine.

In one embodiment, the terminal moieties of the organopolysiloxane are hydrocarbon groups not comprising any heteroatoms (e.g., substantially free from any heteroatoms). Without being bound by theory, it is believed that alkyl end groups of the organopolysiloxanes of the present invention are not as highly degradative or reactive, thus resulting in compositions that are more stable and have a suitably longer shelf-life.

In one embodiment, X is a hydrocarbon moiety not comprising any heteroatoms (e.g., substantially free from any heteroatoms). Although not wishing to be limited by theory, the presence of reactive end groups is believed to result in unstable products that are not shelf-stable, due to their tendency to degrade or react with other materials in the composition over time or to be negatively impacted by destabilizing factors in the use environment.

III. Methods of Making the Organopolysiloxane

Embodiments of the present invention can be made as follows. An amount of amino silicone is added to a clean vessel under inert atmosphere. Optionally, a solvent such as isopropanol or tetrahydrofuran is added. The reaction is optionally mixed and quantities of diamine and difunctional organic compounds capable of reacting with the amino functions of the amine compounds are added, either simultaneously or sequentially. For example, the diamine may be added first and the difunctional organic compound capable of reacting with the amino function added second, to obtain the desired organopolysiloxane. Alternately, these reagents may be added in reverse order.

The reaction is run at a temperature appropriate for the reagents. For example, when the difunctional organic compound capable of reacting with the amino functions is a dichloride, the reaction may be run at relatively higher temperatures (typically above 60° C. and often above 80° C.). Alternately, when the difunctional organic compound capable of reacting with the amino functions is a dibromide, the reaction may be run at relatively lower temperatures, including at room temperature (e.g., 21° C.). Alternately, when the difunctional organic compound capable of reacting with the amino functions is an activated dichloride, the reaction may be run at relatively lower temperatures, including at room temperature (e.g., 21° C.). One of ordinary skill in the art would understand the reaction conditions suitable for the specific difunctional organic compound capable of reacting with the amino functions.

The above making process is also generally described by Lange (U.S. Pat. No. 7,563,856). One skilled in the art would understand how the general process disclosed in Lange can be reapplied to the present development in order to produce the organopolysiloxanes of the present invention.

In one embodiment, the reaction is run without the addition of solvent, resulting in a substantially solvent-free process for making the organopolysiloxane of the present invention.

In another embodiment, the reaction is run and subsequently excess amine is added. Without being bound by theory, it is believed that the excess amine will consume the reactive groups of any residual difunctional organic compounds capable of reacting with the amino functions.

In another embodiment, the reaction mixture is further reacted with an amine containing molecule. Non-limiting examples of such amines include ammonia, methylamine, dimethylamine, trimethylamine or triethylamine. Without being bound by theory it is believed that this further reaction caps un-reacted alkyl-halide functionality.

In another embodiment, the reaction mixture is further reacted with a mono-functional organic species capable of reacting with the amine functionality of the organopolysiloxane. Non-limiting examples of such mono-functional organic species include: methyl bromide, methyl iodide, and ethylbromide. Without being bound by theory it is believed that this further reaction helps to quaternize any residual neutral amine groups of the organopolysiloxane, including the terminal amine functionality.

IV. Adjuncts

The compositions may additionally comprise one or more adjunct materials, as desired for the particular product form. For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

The one or more optional ingredients of the compositions of the current invention might further comprise one or more of the following:

Optional Conditioning Agents—Silicones

Additional conditioning agents, and in particular silicones including non-cationic silicones, may be included in the composition. Conditioning agents include any material which is used to give a particular conditioning benefit to hair and/or skin. In hair treatment compositions, suitable conditioning agents are those which deliver one or more benefits relating to shine, softness, compatibility, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the additional conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

The additional conditioning agent of the compositions of the present invention can be an insoluble silicone conditioning agent. The silicone conditioning agent particles may comprise volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, from about 0.1% to about 8%, from about 0.1% to about 5%, or even from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609. The silicone conditioning agents for use in the compositions of the present invention typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 csk.

The dispersed silicone conditioning agent particles typically have a number average particle diameter ranging from about 0.01 μm to about 50 μm. For small particle application to hair, the number average particle diameters typically range from about 0.01 μm to about 4 μm, from about 0.01 μm to about 2 μm, or even from about 0.01 μm to about 0.5 μm. For larger particle application to hair, the number average particle diameters typically range from about 4 μm to about 50 μm, from about 6 μm to about 30 μm, from about 9 μm to about 20 μm, or even from about 12 μm to about 18 μm.

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

The additional silicone conditioning agent may include an aminosilicone. Aminosilicones, as provided herein, are silicones containing at least one primary amine, secondary amine, tertiary amine, or a quaternary ammonium group. Useful aminosilicones may have less than about 0.5% nitrogen by weight of the aminosilicone, less than about 0.2%, or even less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In one aspect, the aminosilicones used in the present invention have a particle size of less than about 50μ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one embodiment, the aminosilicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This embodiment may also comprise a low viscosity fluid, such as, for example, those materials described below in Section F.(1). The viscosity of aminosilicones discussed herein is measured at 25° C.

In another embodiment, the aminosilicone typically has a viscosity of from about 1,000 cst to about 100,000 cst, from about 2,000 cst to about 50,000 cst, from about 4,000 cst to about 40,000 cst, or even from about 6,000 cst to about 30,000 cs.

The aminosilicone typically is contained in the composition of the present invention at a level by weight of from about 0.05% to about 20%, from about 0.1% to about 10%, and or even from about 0.3% to about 5%.

Other silicone fluids suitable for use in the compositions of the present invention are the insoluble silicone gums and/or resins. Silicone gums are polyorganosiloxane materials having a viscosity, as measured at 25° C., of greater than or equal to 1,000,000 csk. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof. Silicone resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{1/2}$; D denotes the difunctional unit $(CH_3)_2SiO$; T denotes the trifunctional unit $(CH_3)SiO_{3/2}$; and Q denotes the quadra- or tetrafunctional unit $SiO_2$. Primes of the unit symbols (e.g. M', D', T', and Q') denote substituents other than methyl, and must be specifically defined for each occurrence.

In one aspect, silicone resins for use in the compositions of the present invention include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from about 0.5:1.0 to about 1.5:1.0 and the average molecular weight of the silicone resin is typically from about 1000 to about 10,000.

Other non-volatile, insoluble silicone fluid conditioning agents that are suitable for use in the compositions of the present invention are those known as "high refractive index silicones," having a refractive index of at least about 1.46, at least about 1.48, m at least about 1.52, or even at least about 1.55. The refractive index of the polysiloxane fluid will generally be less than about 1.70, typically less than about 1.60. In this context, polysiloxane "fluid" includes oils as well as gums and cyclic silicones. Silicone fluids suitable for use in the compositions of the present invention are disclosed in U.S. Pat. Nos. 2,826,551, 3,964,500, and 4,364,837.

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/0041929A1.

Additional Conditioning Agents—Organic Oils

The compositions of the present invention may also comprise from about 0.05% to about 3%, from about 0.08% to about 1.5%, or even from about 0.1% to about 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about $C_{12}$ to about $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to about $C_{14}$ or even $C_6$ to about $C_{12}$. Suitable fatty esters include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853.

Fatty Alcohols, Acids and/or Esters

The compositions of the present invention can comprise a one or more fatty alcohols, acids and esters. The compositions of the present invention can comprise fatty alcohols, acids and/or esters in an amount from about 0.05% to about 14%, preferably from about 0.5% to about 10%, and more preferably from about 1% to about 8%, by weight of the composition.

Fatty alcohols, acids and/or esters suitable for use in the present invention include those having from about 18 to about 70 carbon atoms, and in one embodiment from about 18 to about 60 carbon atoms, in another embodiment from about 18 to about 50 carbon atoms, in yet another embodiment from about 18 to about 40 carbon atoms, and in even yet another embodiment from about 18 to about 22 carbon atoms. These fatty alcohols, acids and/or esters may be straight or branched chain alcohols and may be saturated or unsaturated.

Non-limiting examples of suitable fatty alcohols include stearyl alcohol, arachidyl alcohol, behenyl alcohol, $C_{21}$ fatty alcohol (1-heneicosanol), $C_{23}$ fatty alcohol (1-tricosanol), $C_{24}$ fatty alcohol (lignoceryl alcohol, 1-tetracosanol), $C_{26}$ fatty alcohol (1-hexacosanol), $C_{28}$ fatty alcohol (1-octacosanol), $C_{30}$ fatty alcohol (1-triacontanol), $C_{20-40}$ alcohols (e.g., Performacol 350 and 425 Alcohols, available from New Phase Technologies), $C_{30-50}$ alcohols (e.g., Performacol 550 Alcohol), $C_{40-60}$ alcohols (e.g., Performacol 700 Alcohol), and mixtures thereof.

Mixtures of different fatty alcohols comprising one or more fatty alcohols having from about 18 to about 70 carbon atoms may also comprise some amount of one or more fatty alcohols or other fatty amphiphiles which have less than about 18 carbon atoms or greater than about 70 carbon atoms and still be considered to be within the scope of the present invention, provided that the resulting dispersed gel network phase has a melt transition temperature of at least about 38° C. Such fatty alcohols suitable for use in the present invention may be of natural or vegetable origin, or they may be of synthetic origin.

Gel Matrix

In some embodiments, the fatty alcohols, may be present in the form of a dispersed gel network phase (i.e., as a phase which is incorporated and dispersed into the final composition). In one embodiment, a secondary cationic surfactant, together with high melting point fatty compounds and an aqueous carrier, form a gel matrix. The gel matrix is suitable for providing various conditioning benefits such as slippery feel during the application to wet hair and softness and moisturized feel on dry hair.

The compositions of the present invention can comprise a dispersed fatty alcohol gel network phase in an amount greater than about 0.1%, preferably from about 1% to about 60%, and more preferably from about 5% to about 40%, by weight of the composition.

The gel network component of the present invention can comprise a secondary surfactant. As used herein, "secondary surfactant" refers to one or more surfactants which are combined with the fatty alcohol and water to form the gel network of the present invention as a pre-mix separate from the other components of the shampoo composition. The secondary surfactant is separate from and in addition to any emulsifying surfactant and/or any surfactant of the personal care composition. However, the secondary surfactant may be the same or different type of surfactant or surfactants as that or those selected for the surfactant component described above.

The compositions of the present invention can comprise secondary surfactant as part of the pre-formed dispersed gel network phase in an amount from about 0.01% to about 15%, preferably from about 0.1% to about 10%, and more preferably from about 0.3% to about 5%, by weight of the shampoo composition.

Suitable secondary surfactants include anionic, zwitterionic, amphoteric, cationic, and nonionic surfactants. Preferably, the secondary surfactant is selected from anionic, cationic, and nonionic surfactants, and mixtures thereof. For additional discussion of secondary surfactants which are suitable for use in the present invention, see U.S. 2006/0024256 A1.

Additionally, in an embodiment of the present invention, certain secondary surfactants which have a hydrophobic tail group with a chain length of from about 16 to about 22 carbon atoms may be selected to contribute to obtaining a melt transition temperature of at least about 38 deg. C. for the resulting dispersed gel network phase. For such secondary surfactants, the hydrophobic tail group may be alkyl, alkenyl (containing up to 3 double bonds), alkyl aromatic, or branched alkyl. In such an embodiment, it is preferred that the secondary surfactant is present in the gel network component relative to the fatty alcohol at a weight ratio from about 1:5 to about 5:1. Mixtures of more than one surfactant of the above specified types may be used for the secondary surfactant of the present invention.

In one embodiment of the gel matrix, the secondary surfactant may be a cationic surfactant and the cationic secondary surfactant and the high melting point fatty compound may be contained at a level such that the weight ratio of the cationic surfactant to the high melting point fatty compound is in the range of from about 1:1 to about 1:10, or even from about 1:1 to about 1:6.

The gel network component may also comprise water or suitable solvents. The water or suitable solvent and the secondary surfactant together contribute to the swelling of the fatty alcohol. This, in turn, leads to the formation and the stability of the gel network. As used herein, the term "suitable solvent" refers to any solvent which can be used in the place of or in combination with water in the formation of the gel network of the present invention.

The compositions of the present invention comprise water or suitable solvents as part of the pre-formed dispersed gel network phase in an amount suitable to achieve a gel network when combined with fatty alcohol and secondary surfactant according to the present invention. In one embodiment, the compositions of the present invention comprise as part of the pre-formed dispersed gel network phase at least about 0.05% of water or a suitable solvent, by weight of the shampoo composition. In another embodiment, the compositions comprise water or a suitable solvent as part of the pre-formed dispersed gel network phase is an amount relative to the amount of fatty alcohol at a weight ratio of at least about 1:1.

Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

Humectants

The compositions of the present invention may contain a humectant. The humectants herein are selected from the group consisting of polyhydric alcohols, water soluble alkoxylated nonionic polymers, and mixtures thereof. The humectants, when used herein, are typically used at levels of from about 0.1% to about 20%, or even from about 0.5% to about 5%.

Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals.

The composition may comprise from about 0.001% to about 10%, alternatively from about 0.01% to about 5%, of at least one vitamin. Herein, "vitamins" means vitamins, pro-vitamins, and their salts, isomers and derivatives. Non-limiting examples of suitable vitamins include: vitamin B compounds (including $B_1$ compounds, $B_2$ compounds, $B_3$ compounds such as niacinamide, niacinnicotinic acid, tocopheryl nicotinate, $C_1$-$C_{18}$ nicotinic acid esters, and nicotinyl alcohol; $B_5$ compounds, such as panthenol or "pro-$B_5$", pantothenic acid, pantothenyl; $B_6$ compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition may comprise a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu-HGG, also known as IAMIN®). The compositions may comprise from about $1 \times 10^{-7}\%$ to about 20%, alternatively from about $1 \times 10^{-6}\%$ to about 10%, and alternatively from about $1 \times 10^{-5}\%$ to about 5% of the peptide.

The composition may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). Other sugar amine compounds useful in skin care compositions include those described in U.S. Pat. No. 6,159,485, issued to Yu, et al. In one embodiment, the composition may comprise from about 0.01% to about 15%, alternatively from about 0.1% to about 10%, and alternatively from about 0.5% to about 5%, of the sugar amine.

The composition may comprise one or more sunscreen actives (or sunscreen agents) and/or ultraviolet light absorbers. Herein, suitable sunscreen actives include oil-soluble sunscreens, insoluble sunscreens, and water-soluble sunscreens. In certain embodiments, the composition may comprise from about 1% to about 20%, or, alternatively, from about 2% to about 10%, by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Non-limiting examples of suitable oil-soluble sunscreens include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof.

Non-limiting examples of suitable insoluble sunscreens include methylene bis-benzotriazolyl tetramethylbutyl-phenol, titanium dioxide, zinc cerium oxide, zinc oxide, and derivatives and mixtures thereof.

Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

The composition may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

The composition may comprise a tanning active. The compositions may comprise from about 0.1% to about 20%, from about 2% to about 7%, or, alternatively, from about 3% to about 6%, by weight of the composition, of a tanning active. A suitable tanning active includes dihydroxyacetone, which is also known as DHA or 1,3-dihydroxy-2-propanone.

The composition may comprise a safe and effective amount of one or more anti-acne actives. Examples of useful anti-acne actives include resorcinol, sulfur, salicylic acid, erythromycin, zinc, and benzoyl peroxide. Suitable anti-acne actives are described in further detail in U.S. Pat. No. 5,607,980. The composition may comprise a safe and effective amount of a desquamation active such as from about 0.01% to about 10%, from about 0.5% to about 5%, or, alternatively, from about 0.1% to about 2%, by weight of the composition. For example, the desquamation actives tend to improve the texture of the skin (e.g., smoothness). A suitable desquamation system may comprise sulfhydryl compounds and zwitterionic surfactants and is described in U.S. Pat. No. 5,681,852. Another suitable desquamation system may comprise salicylic acid and zwitterionic surfactants and is described in U.S. Pat. No. 5,652,228.

The composition may comprise a safe and effective amount of an anti-cellulite agent. Suitable agents may include, but are not limited to, xanthine compounds (e.g., caffeine, theophylline, theobromine, and aminophylline).

Skin care compositions may comprise a safe and effective amount of a chelating agent such as from about 0.1% to about 10% or from about 1% to about 5% of the composition. Exemplary chelators are disclosed in U.S. Pat. No. 5,487,884. A suitable chelator is furildioxime and derivatives.

The composition may comprise a skin lightening agent. The compositions may comprise from about 0.1% to about 10%, from about 0.2% to about 5%, or, alternatively, from about 0.5% to about 2%, by weight of the composition, of a skin lightening agent. Suitable skin lightening agents include kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, and the like. Other suitable skin lightening materials include undecylenoyl phenylalanine (Sepiwhite® from SEPPIC), aloesin, Actiwhite® (Cognis), and Emblica® (Rona).

The composition compositions may comprise a flavonoid. The flavonoid can be synthetic materials or obtained as extracts from natural sources, which also further may be derivatized. Examples of classes of suitable flavonoids are disclosed in U.S. Pat. No. 6,235,773.

The composition may comprise protease inhibitors including, but are not limited to, hexamidine compounds, vanillin acetate, menthyl anthranilate, soybean trypsin inhibitor, Bowman-Birk inhibitor, and mixtures thereof. Skin care compositions can include hexamidine compounds, its salts, and derivatives. As used herein, "hexaminide compound" means a compound having the formula:

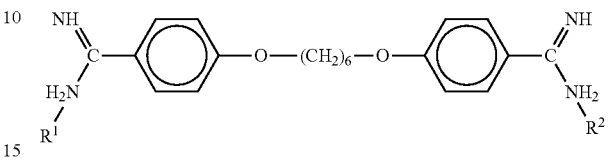

wherein $R^1$ and $R^2$ are optional or are organic acids (e.g., sulfonic acids, etc.). A particularly suitable hexamidine compound is hexamidine diisethionate.

The composition may other optional components such as non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobial or antifungal actives, and other useful skin care actives, which are described in further detail in U.S. application publication No. US 2006/0275237A1 and US 2004/0175347A1.3.

Pigments

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names.

Surfactants

The compositions of the present invention may comprise one or more surfactants. The surfactant component is included in personal care compositions of the present invention to provide cleansing performance. The surfactant may be selected from anionic surfactant, zwitterionic or ampho-teric surfactant, or a combination thereof. The concentration of the surfactant component in the composition should be sufficient to provide the desired cleaning and lather performance, and generally range from about 5% to about 50%.

Suitable surfactant components for use in the composition herein include those which are known for use in hair care, fabric care, surface care or other personal care and/or home care cleansing compositions. The concentration of the surfactant component in the composition should be sufficient to provide the desired cleaning and lather performance.

Suitable anionic surfactants useful in the current invention are generally used in a range from about 5% to about 50%, preferably from about 8% to about 30%, more preferably from about 10% to about 25%, even more preferably from about 12% to about 22%, by weight of the composition.

Suitable zwitterionic or amphoteric surfactants for use in the composition herein include those which are known for use in hair care or other personal cleansing compositions. Concentration of such amphoteric surfactants preferably ranges from about 0.5% to about 20%, preferably from about 1% to about 10%. Non-limiting examples of suitable zwitterionic or amphoteric surfactants are described in U.S. Pat. Nos. 5,104,646 and 5,106,609, both to Bolich Jr. et al.

The compositions of the present invention may further comprise additional surfactants for use in combination with the anionic, zwitterionic or amphoteric surfactant component described hereinbefore. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, or even from about 0.3% to about 5.0%.

Fabric Softening Active Compounds

The fabric or home care compositions of the current invention may comprise a fabric softening active. Said fabric softening active may comprise, as the principal active, compounds of the following formula:

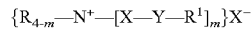

wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X may independently be $(CH_2)_n$, $CH_2$—CH($CH_3$)— or CH—($CH_3$)—$CH_2$—; each Y may comprise —O—(O)C—, —C(O)—O—, —NR—C(O)—, or —C(O)—NR—; each m may be 2 or 3; each n may be from 1 to about 4, in one aspect 2; the sum of carbons in each $R^1$, plus one when Y is —O—(O)C— or —NR—C(O)—, may be $C_{12}$-$C_{22}$, or $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

In another aspect, the fabric softening active may comprise the general formula:

$[R_3N^+CH_2CH(YR^1)(CH_2YR^1)]X^-$ wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X may independently be $(CH_2)_n$, $CH_2$—CH($CH_3$)— or CH—($CH_3$)—$CH_2$—; each Y may comprise —O—(O)C—, —C(O)—O—, —NR—C(O)—, or —C(O)—NR—; each m may be 2 or 3; each n may be from 1 to about 4, in one aspect 2; the sum of carbons in each $R^1$, plus one when Y is —O—(O)C— or —NR—C(O)—, may be $C_{12}$-$C_{22}$, or $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

Such compounds include those having the formula:

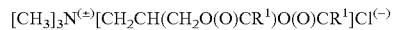

wherein each R may comprise a methyl or ethyl group. In one aspect, each $R^1$ may comprise a $C_{15}$ to $C_{19}$ group. As used herein, when the diester is specified, it can include the monoester that is present.

These types of agents and general methods of making them are disclosed in U.S. Pat. No. 4,137,180. An example of a suitable "propyl" ester quaternary ammonium fabric softener active comprising the formula 1,2-di(acyloxy)-3-trimethylammoniopropane chloride.

In one aspect, the fabric softening active may comprise the formula:

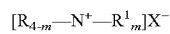

wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X may independently be $(CH_2)_n$, $CH_2$—CH($CH_3$)— or CH—($CH_3$)—$CH_2$—; each Y may comprise —O—(O)C—, —C(O)—O—, —NR—C(O)—, or —C(O)—NR—; each m may be 2 or 3; each n may be from 1 to about 4, in one aspect 2; the sum of carbons in each $R^1$, plus one when Y is —O—(O)C— or —NR—C(O)—, may be $C_{12}$-$C_{22}$, or $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

In a further aspect, the fabric softening active may comprise the formula:

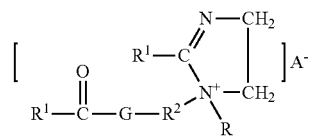

wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate; $R^2$ may comprise a $C_{1-6}$ alkylene group, in one aspect an ethylene group; and G may comprise an oxygen atom or an —NR— group.

In a yet further aspect, the fabric softening active may comprise the formula:

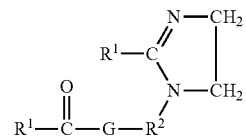

wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; $R^2$ may comprise a $C_{1-6}$ alkylene group, in one aspect an ethylene group; and G may comprise an oxygen atom or an —NR— group.

In a further aspect, the fabric softening active may comprise condensation reaction products of fatty acids with dialkylenetriamines in, e.g., a molecular ratio of about 2:1.

Non-limiting examples of such fabric softening actives include are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate.

It will be understood that combinations of softener actives disclosed above are suitable for use herein.

It can be understood by one of skill in the art that the cationic optional fabric softener actives herein further comprise counter ions such as anions, that provide electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, and the like. In one aspect, the anion may comprise chloride or methylsulfate. The anion, in some aspects, may carry a double or multiple charge.

In one aspect, the fabric care and/or treatment composition may comprise a second softening agent selected from the group consisting of polyglycerol esters (PGEs), oily sugar derivatives, and wax emulsions. Suitable PGEs include those disclosed in U.S. PA 61/089,080. Suitable oily sugar derivatives and wax emulsions include those disclosed in USPA 2008-0234165 A1.

In one aspect, the compositions may comprise from about 0.001% to about 0.01% of an unsaturated aldehyde. In one aspect, the compositions are essentially free of an unsaturated aldehyde. Without being limited by theory, in this aspect, the compositions are less prone to the yellowing effect often encountered with amino-containing agents.

Perfume

The optional perfume component may comprise a component selected from the group consisting of perfume oils, mixtures of perfume oils, perfume microcapsules, pressure-activated perfume microcapsules, moisture-activated perfume microcapsules and mixtures thereof. Said perfume microcapsule compositions may comprise from about 0.05% to about 5%; or from about 0.1% to about 1% of an encapsulating material. In turn, the perfume core may comprise a perfume and optionally a diluent.

Pressure-activated perfume microcapsules generally comprise core-shell configurations in which the core material further comprises a perfume oil or mixture of perfume oils. The shell material surrounding the core to form the microcapsule can be any suitable polymeric material which is impervious or substantially impervious to the materials in the core (generally a liquid core) and the materials which may come in contact with the outer substrate of the shell. In one aspect, the material making the shell of the microcapsule may comprise formaldehyde. Formaldehyde based resins such as melamine-formaldehyde or urea-formaldehyde resins are especially attractive for perfume encapsulation due to their wide availability and reasonable cost.

Moisture-activated perfume microcapsules, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;

(1) a pro-perfume;
(2) a low odor detection threshold perfume ingredients, wherein said low odor detection threshold perfume ingredients may comprise less than about 25%, by weight of the total neat perfume composition; and
(3) mixtures thereof.

A suitable moisture-activated perfume carrier that may be useful in the disclosed multiple use fabric conditioning composition may comprise cyclodextrin. As used herein, the term "cyclodextrin" includes any of the known cyclodextrins such as unsubstituted cyclodextrins containing from six to twelve glucose units, especially beta-cyclodextrin, gamma-cyclodextrin, alpha-cyclodextrin, and/or derivatives thereof, and/or mixtures thereof. A more detailed description of suitable cyclodextrins is provided in U.S. Pat. No. 5,714,137. Suitable cylodextrins herein include beta-cyclodextrin, gamma-cyclodextrin, alpha-cyclodextrin, substituted beta-cyclodextrins, and mixtures thereof. In one aspect, the cyclodextrin may comprise beta-cyclodextrin. Perfume molecules are encapsulated into the cavity of the cyclodextrin molecules to form molecular microcapsules, commonly referred to as cyclodextrin/perfume complexes. The perfume loading in a cyclodextrin/perfume complex may comprise from about 3% to about 20%, or from about 5% to about 18%, or from about 7% to about 16%, by weight of the cyclodextrin/perfume complex.

The cyclodextrin/perfume complexes hold the encapsulated perfume molecules tightly, so that they can prevent perfume diffusion and/or perfume loss, and thus reducing the odor intensity of the multiple use fabric conditioning composition. However, the cyclodextrin/perfume complex can readily release some perfume molecules in the presence of moisture, thus providing a long lasting perfume benefit. Non-limiting examples of preparation methods are given in U.S. Pat. Nos. 5,552,378, and 5,348,667.

Deposition Aids/Enhancing Agents

The composition of the present invention can optionally comprise from about 0.01% to about 10%, from about 0.05 to about 5%, or from about 0.15 to about 3% of a deposition aid. Suitable deposition aids are disclosed in, for example, U.S. patent application Ser. No. 12/080,358.

In one aspect, the deposition aid may be a cationic or amphoteric polymer. In another aspect, the deposition aid may be a cationic polymer. Cationic polymers in general and their method of manufacture are known in the literature. In one aspect, the cationic polymer may have a cationic charge density of from about 0.005 meq/g to about 23 meq/g, from about 0.01 meq/g to about 12 meq/g, or from about 0.1 meq/g to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

Non-limiting examples of deposition enhancing agents are cationic or amphoteric, polysaccharides, proteins and synthetic polymers. Cationic polysaccharides include cationic cellulose derivatives, cationic guar gum derivatives, chitosan and derivatives and cationic starches. Cationic polysaccharides have a molecular weight from about 50,000 to about 2 million, or even from about 100,000 to about 3,500,000. Suitable cationic polysaccharides include cationic cellulose ethers, particularly cationic hydroxyethylcellulose and cationic hydroxypropylcellulose. Examples of cationic hydroxyalkyl cellulose include those with the INCI name Polyquaternium 10 such as those sold under the trade names Ucare™ Polymer JR 30M, JR 400, JR 125, LR 400 and LK 400 polymers; Polyquaternium 67 such as those sold under the trade name Softcat SK™, all of which are marketed by Amerchol Corporation, Edgewater N.J.; and Polyquaternium 4 such as those sold under the trade name Celquat™ H200 and Celquat™ L-200 available from National Starch and Chemical Company, Bridgewater, N.J. Other suitable polysaccharides include Hydroxyethyl cellulose or hydroxypropylcellulose quaternized with glycidyl $C_{12}$-$C_{22}$ alkyl dimethyl ammonium chloride. Examples of such polysaccharides include the polymers with the INCI names Polyquaternium 24 such as those sold under the trade name Quaternium LM 200 by Amerchol Corporation, Edgewater N.J. Cationic starches described by D. B. Solarek in Modified Starches, Properties and Uses published by CRC Press (1986) and in U.S. Pat. No. 7,135,451, col. 2, line 33-col. 4, line 67. Cationic galactomannans include cationic guar gums or cationic locust bean gum. An example of a cationic guar gum is a quaternary ammonium derivative of Hydroxypropyl Guar such as those sold under the trade name Jaguar C13 and Jaguar Excel available from Rhodia, Inc of Cranbury N.J. and N-Hance by Aqualon, Wilmington, Del.

Another group of suitable cationic polymers includes those produced by polymerization of ethylenically unsaturated monomers using a suitable initiator or catalyst, such as those disclosed in U.S. Pat. No. 6,642,200.

Suitable polymers may be selected from the group consisting of cationic or amphoteric polysaccharide, polyethylene imine and its derivatives, and a synthetic polymer made by polymerizing one or more cationic monomers selected from the group consisting of N,N-dialkylaminoalkyl acrylate, N,N-dialkylaminoalkyl methacrylate, N,N-dialkylaminoalkyl acrylamide, N,N-dialkylaminoalkylmethacrylamide, quaternized N,N dialkylaminoalkyl acrylate quaternized N,N-dialkylaminoalkyl methacrylate, quaternized N,N-dialkylaminoalkyl acrylamide, quaternized N,N-dialkylaminoalkylmethacrylamide, Methacryloamidopropyl-pentamethyl-1,3-propylene-2-ol-ammonium dichloride, N,N,N,N', N',N'',N''-heptamethyl-N''-3-(1-oxo-2-methyl-2-propenyl) aminopropyl-9-oxo-8-azo-decane-1,4,10-triammonium trichloride, vinylamine and its derivatives, allylamine and its derivatives, vinyl imidazole, quaternized vinyl imidazole and diallyl dialkyl ammonium chloride and combinations thereof, and optionally a second monomer selected from the group consisting of acrylamide, N,N-dialkyl acrylamide, methacrylamide, N,N-dialkylmethacryl amide, C1-C12 alkyl acrylate, C1-C12 hydroxyalkyl acrylate, polyalkylene glyol acrylate, C1-C12 alkyl methacrylate, C1-C12 hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and derivatives, acrylic acid, methacrylic acid, maleic acid, vinyl sulfonic acid, styrene sulfonic acid, acrylamidopropylmethane sulfonic acid (AMPS) and their salts. The polymer may optionally be branched or cross-linked by using branching and crosslinking monomers. Branching and crosslinking monomers include ethylene glycoldiacrylate divinylbenzene, and butadiene. In another aspect, the treatment composition may comprise an amphoteric deposition aid polymer so long as the polymer possesses a net positive charge. Said polymer may have a cationic charge density of about 0.05 to about 18 milliequivalents/g.

In another aspect, the deposition aid may be selected from the group consisting of cationic polysaccharide, polyethylene imine and its derivatives, poly(acrylamide-co-diallyldimethylammonium chloride), poly(acrylamide-methacrylamidopropyltrimethyl ammonium chloride), poly (acrylamide-co-N,N-dimethyl aminoethyl acrylate) and its quaternized derivatives, poly(acrylamide-co-N,N-dimethyl aminoethyl methacrylate) and its quaternized derivative, poly(hydroxyethylacrylate-co-dimethyl aminoethyl methacrylate), poly(hydroxpropylacrylate-co-dimethyl aminoethyl methacrylate), poly(hydroxypropylacrylate-co-methacrylamidopropyltrimethylammonium chloride), poly (acrylamide-co-diallyldimethylammonium chloride-co-acrylic acid), poly(acrylamide-methacrylamidopropyltrimethyl ammonium chloride-co-acrylic acid), poly(diallyldimethyl ammonium chloride), poly(vinylpyrrolidone-co-dimethylaminoethyl methacrylate), poly(ethyl methacrylate-co-quaternized dimethylaminoethyl methacrylate), poly(ethyl methacrylate-co-oleyl methacrylate-co-diethylaminoethyl methacrylate), poly(diallyldimethylammonium chloride-co-acrylic acid), poly(vinyl pyrrolidone-co-quaternized vinyl imidazole) and poly (acrylamide-co-Methacryloamidopropyl-pentamethyl-1,3-propylene-2-ol-ammonium dichloride), Suitable deposition aids include Polyquatemium-1, Polyquaternium-5, Polyquaternium-6, Polyquaternium-7, Polyquaternium-8, Polyquatemium-11, Polyquaternium-14, Polyquaternium-22, Polyquatemium-28, Polyquaternium-30, Polyquaternium-32 and Polyquaternium-33, as named under the International Nomenclature for Cosmetic Ingredients.

In one aspect, the deposition aid may comprise polyethyleneimine or a polyethyleneimine derivative. A suitable polyethyleneinine useful herein is that sold under the trade name Lupasol® by BASF, AG, and Ludwigshafen, Germany.

In another aspect, the deposition aid may comprise a cationic acrylic based polymer. In a further aspect, the deposition aid may comprise a cationic polyacrylamide. In another aspect, the deposition aid may comprise a polymer comprising polyacrylamide and polymethacrylamidopropyl trimethylammonium cation. In another aspect, the deposition aid may comprise poly(acrylamide-N-dimethyl aminoethyl acrylate) and its quaternized derivatives. In this aspect, the deposition aid may be that sold under the trade name Sedipur®, available from BTC Specialty Chemicals, a BASF Group, Florham Park, N.J. In a yet further aspect, the deposition aid may comprise poly(acrylamide-co-methacrylamidopropyltrimethyl ammonium chloride). In another aspect, the deposition aid may comprise a non-acrylamide based polymer, such as that sold under the trade name Rheovis® CDE, available from Ciba Specialty Chemicals, a BASF group, Florham Park, N.J., or as disclosed in USPA 2006/0252668.

In another aspect, the deposition aid may be selected from the group consisting of cationic or amphoteric polysaccharides. In one aspect, the deposition aid may be selected from the group consisting of cationic and amphoteric cellulose ethers, cationic or amphoteric galactomannan, cationic guar gum, cationic or amphoteric starch, and combinations thereof.

Another group of suitable cationic polymers may include alkylamine-epichlorohydrin polymers which are reaction products of amines and oligoamines with epichlorohydrin, for example, those polymers listed in, for example, U.S. Pat. Nos. 6,642,200 and 6,551,986. Examples include dimethylamine-epichlorohydrin-ethylenediamine, available under the trade name Cartafix® CB and Cartafix® TSF from Clariant, Basle, Switzerland.

Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin. They are available from Hercules Inc. of Wilmington Del. under the trade name Kymene™ or from BASF AG (Ludwigshafen, Germany) under the trade name Luresin™. The cationic polymers may contain charge neutralizing anions such that the overall polymer is neutral under ambient conditions. Non-limiting examples of suitable counter ions (in addition to anionic species generated during use) include chloride, bromide, sulfate, methylsulfate, sulfonate, methylsulfonate, carbonate, bicarbonate, formate, acetate, citrate, nitrate, and mixtures thereof.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. In one aspect, the MW of the cationic polymer may be from about 500 Daltons to about 37,500 Daltons.

Builders

The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other suitable polycarboxylates for use herein are the polyacetal carboxylates described in U.S. Pat. Nos. 4,144,226 and 4,246,495. Other polycarboxylate builders are the oxydisuccinates and the ether carboxylate builder compositions comprising a combination of tartrate monosuccinate and tartrate disuccinate described in U.S. Pat. No. 4,663,071, Builders for use in liquid detergents are described in U.S. Pat. No. 4,284,532, One suitable builder includes may be citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites. Such materials and their use as detergent builders are more fully discussed in U.S. Pat. No. 4,605,509.

Dispersants

The compositions may contain from about 0.1%, to about 10%, by weight of dispersants Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives thereof such as those described in U.S. Pat. Nos. 4,597,898, 4,676,921, 4,891,160, 4,659,802 and 4,661,288.

Enzymes

The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents

The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant

The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners

The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach System

Bleach systems suitable for use herein contain one or more bleaching agents. Non-limiting examples of suitable bleaching agents include catalytic metal complexes; activated peroxygen sources; bleach activators; bleach boosters;

photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Suitable bleach boosters include those described in U.S. Pat. No. 5,817,614. Other bleaching agents include metal complexes of transitional metals with ligands of defined stability constants. Such catalysts are disclosed in U.S. Pat. Nos. 4,430,243, 5,576,282, 5,597,936 and 5,595,967.

Stabilizer

The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

V. Consumer Product Composition Comprising Benefit Agent Emulsion

Applicants have observed that when making the consumer product, the order in which the ingredients are mixed can affect the final composition's deposition performance. Although not wishing to be bound by theory, it is believed that in order for a cationic deposition aid to function most efficiently, it must first adsorb onto the benefit agent. Emulsifying the cationic deposition aid with the hydrophobic benefit agent allows the deposition aid to pre-adsorb onto the benefit agent before these ingredients are incorporated into the balance of ingredients in the auxiliary composition which can contain anionic surfactant.

Given that most cleansing products contain relatively high amounts of anionic surfactants but relatively low levels of benefit agents and deposition aid, binding of the deposition aid onto the benefit agent may be problematic if these ingredients are added separately to compositions that may include ingredients such as anionic surfactants. For example, factors such as high concentration of anionic surfactants and strong interaction (electrostatic) between an anionic surfactant and a cationic deposition polymer are likely to favor association between the anionic surfactant and the cationic deposition polymer over that between the weakly interacting, low-level cationic polymer and hydrophobic benefit agent.

Further, since the amount of anionic surfactant likely to adsorb on the hydrophobic benefit agent would be much smaller than the amount of the surfactant remaining dissolved (i.e., non-adsorbed) in the solution-phase, the cationic deposition polymer is most likely to associate/form complexes (i.e., anionic complexes in anionic surfactant-rich solutions) with the dissolved surfactant molecules rather than with any surfactant molecules pre-adsorbed on the benefit agent. Being present at a much higher concentration than any cationic polymer-anionic surfactant complex that could potentially form, the anionic surfactant may adsorb to the hydrophobic benefit agent far more easily than to the polymer-surfactant complex, such that the cationic deposition polymer may not be able to adsorb to the benefit agent to any considerable extent. Thus, when these two materials are added separately as ingredients to anionic surfactant-rich cleansing product compositions, the hydrophobic benefit agent may simply dissolve in the surfactant-rich solution.

It is often theorized in the art that association between the cationic deposition polymer and the hydrophobic benefit agent is achieved only when the cleansing products get heavily diluted during the course of the rinsing process. However, in this scenario, large portions of the added deposition polymer and the benefit agent would be rinsed off before the optimum dilution level is reached.

In order to efficiently deliver the end-use benefits (e.g., hair-conditioning, fabric-softening, fragrance-extension) of the hydrophobic benefit agents, the benefit agent must not only substantially deposit on the treated substrate, but it must also be available in a physical form that is suitable for providing the desired end-use benefit. For example, deposition of a hydrophobic substance such as silicone on the hair or on a fabric causes hydrophobic-modification of the hair or the fabric surface, which in turn leads to effects that manifest as hair-conditioning or fabric-softening benefits.

In one aspect, the present invention provides a benefit agent emulsion comprising a benefit agent and a cationic deposition aid bonded to the surface of the benefit agent. In one aspect, the benefit agent is hydrophobic. In a particular aspect, the emulsion is substantially free of surfactant.

In another aspect, the invention provides a method for making a cleansing or surface-conditioning consumer product composition. The method comprises: (a) providing the benefit agent emulsion; (b) providing an auxiliary composition; and (c) combining said emulsion and said auxiliary composition to form the consumer product composition. The auxiliary composition comprises the balance of ingredients which, in combination with the emulsion, form the final consumer product composition. The auxiliary composition can comprise one or more separate compositions, which can be combined with the emulsion either separately or together to form the final consumer product. In particular embodiments, the auxiliary composition comprises a solvent (e.g., a hydrophilic solvent such as water) and/or surfactant, as well as any other desired ingredients.

Adsorption between the benefit agent (e.g., hydrophobic benefit agent) and the cationic deposition aid is achieved in the emulsion composition prior to its addition to the auxiliary composition. Pre-adsorbing the deposition aid to the benefit agent promotes deposition efficiency and dispersion stability (i.e., against flocculation and coalescence) of the emulsion components when the emulsion is dispersed in aqueous or other hydrophilic solutions, especially those comprising surfactant.

In particular embodiments, the benefit agent can be encapsulated within a capsule-like enclosure; in other embodiments, the benefit agent is not encapsulated. Encapsulation can limit the amount of benefit agent available for surface treatment, yet can also prevent adverse interactions between the benefit agent and other ingredients. Thus, the desirability of encapsulation will depend upon, for example, the level of benefit agent that can diffuse through the capsule wall or leak due to breakage, versus the consequences of adverse ingredient interactions.

In one aspect, the emulsion is in the form of an oil-in-water emulsion, wherein the emulsion comprises at least one hydrophobic liquid, which can be the benefit agent or can be in addition to the benefit agent. The hydrophobic benefit agent can be homogenously dispersed in the hydrophobic liquid. For instance, in one embodiment the emulsion is in the form of an emulsified oil droplet in an oil-in-water emulsion, wherein the deposition-aid serves as an emulsifier for emulsifying the benefit agent phase in a water phase, prior to mixing the oil-in-water emulsion (i.e., emulsion) with the auxiliary composition.

In one embodiment, the surfactant can be selected from the group consisting of anionic, non-ionic, zwitterionic, cationic, amphoteric, and mixtures thereof. In particular embodiments, the surfactant comprises anionic surfactant.

In one embodiment, the hydrophobic benefit agent is selected from the group consisting of silicone, fragrance, emollient, antimicrobial agent, sunscreen, lipid, oil, hydrocarbon, wax, hydrophobically-modified pigment, inorganic compound, and mixtures thereof.

In another aspect, the invention provides a method of depositing a benefit agent onto a substrate comprising contacting the substrate with the emulsion, which can be delivered in the form of the consumer product composition. In another aspect, the invention provides a method of providing hair conditioning, skin moisturizing, fabric softening, or a fabric anti-wrinkle property comprising contacting the finished consumer product composition with a substrate selected from the group consisting of hair, skin, and fabric.

Consumer product compositions described herein are suitable for use as cleansing and/or surface-conditioning products like shampoos, body-washes, liquid soaps, laundry detergents, and fabric softeners, which allow substantive deposition and retention on the hair, skin, and fabric of one or more benefit agents, desirably hydrophobic benefit agents, contained therein.

In one embodiment, the hydrophobic benefit agent and the cationic polymer deposition aid are simply mixed together using techniques known in the art in order to form the emulsion of the present invention. Optionally, hydrophilic solvent and/or other ingredients that do not interfere with the adsorption of the deposition aid to the hydrophobic benefit agent can also be present in the emulsion.

The hydrophobic benefit agent can be any suitable agent for the desired end-use benefit. For example, the benefit agent can be selected from the group consisting of silicone, fragrance, emollient, antimicrobial agent, sunscreen, lipid, oil, hydrocarbon, wax, hydrophobically-modified pigment, inorganic compound, and mixtures thereof.

In one embodiment, the hydrophobic benefit agent and/or the emulsion is prepared in the form of an oil-in-water (O/W) emulsion. In a particular embodiment, the hydrophobic benefit agent of the emulsion is homogenously dispersed in a hydrophobic liquid. In another embodiment, the hydrophobic benefit agent itself serves as the hydrophobic liquid.

The cationic polymer deposition aid can serve as the emulsifier for emulsifying the benefit agent phase in a hydrophilic phase, such as a water phase. Alternatively, an alternate emulsifier can be used to emulsify the hydrophobic benefit agent with the hydrophilic (e.g., water) phase. For example, in some embodiments the benefit agent emulsifier can comprise a water-insoluble particulate material comprising a surface-active or a water-insoluble anionic polymer. In one embodiment, an anionic polymer is included in the range of 0.1% to 5% by weight, based on the weight of the oil-phase of the oil-in-water emulsion. Alternatively in some embodiments, the emulsifier can comprise a water-soluble, high molecular weight cationic polymer that is insoluble in anionic surfactant solutions. High-shear mixing methods as known in the art can be used to form the emulsions contemplated herein.

Optional ingredients that do not adversely affect the adsorption of the hydrophobic benefit agent (or the emulsified hydrophobic benefit agent) to the cationic polymer deposition aid can also be included in the emulsions and/or emulsion, depending upon the particular attributes desired in the end-use consumer product.

In order to form the finished consumer product composition, the emulsion is combined with the auxiliary composition comprising surfactant. In one embodiment, the consumer product compositions comprise from 0.5% to 95% by weight of surfactant. In some embodiments, the surfactant comprises anionic surfactant. Desired optional ingredients can be included in the auxiliary composition, the emulsion if they are compatible therewith, or can be added separately to the consumer product composition. Mixing methods as known in the art can be used to form the consumer product compositions herein.

The consumer product composition can be in any desired form. For instance, the composition form can be selected from the group consisting of shampoo, bodywash, detergent, antimicrobial wash, and hard surface cleaner.

The present invention also provides a method of depositing a hydrophobic benefit agent onto a substrate, such as hair, skin, or fabric, comprising contacting the substrate with the consumer product composition of the present invention. Such consumer products can deliver benefits such as hair conditioning, skin moisturizing, fabric softening, or a fabric anti-wrinkle property.

Product Forms
Personal Care Compositions

In one aspect, the consumer products disclosed herein may be personal care compositions. Such compositions can be applied to the skin and/or hair in order to provide cleansing and/or conditioning treatment. The compositions can be, for example, formulated as bars, liquids, emulsions, shampoos, gels, powders, sticks, hair conditioners (rinse off or leave in), hair tonics, pastes, hair colorants, sprays, mousses and other styling products.

Fabric and/or Home Care Cleaning and/or Treatment Compositions

In one aspect, the consumer products disclosed herein may be fabric and/or home care compositions. Such compositions can be applied to the fabrics, hard surfaces, ceramics, glass, wood, and the like in order to provide cleansing and/or conditioning treatment. The compositions can be formulated as bars, liquids, emulsions, gels, powders, sticks, pastes, sprays, mousses and the like.

Aspects of the invention include the use of the organosilicone polymers disclosed herein in laundry detergent compositions (e.g., TIDE™), hard surface cleaners (e.g., MR CLEAN™) automatic dishwashing liquids (e.g., CASCADE™), dishwashing liquids (e.g., DAWN™), and floor cleaners (e.g., SWIFFER™). Non-limiting examples of cleaning compositions may include those described in U.S.

Pat. Nos. 4,515,705; 4,537,706; 4,537,707; 4,550,862; 4,561,998; 4,597,898; 4,968,451; 5,565,145; 5,929,022; 6,294,514; and 6,376,445.

The fabric or home care compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

VI. Method of Making Compositions

Any suitable method of making the composition of the present invention may be used. In one embodiment, the organopolysiloxane conditioning polymer is blended with the other ingredients present in the composition. In an alternate embodiment, the organopolysiloxane of the present invention is pre-emulsified, optionally with other ingredients that do not adversely adsorb onto the organopolysiloxane conditioning polymer, then blended with the other components of the finished composition, according to standard methods known in the art. The typical procedure for pre-emulsified embodiments involves pre-emusifying the organopolysiloxane conditioning agent with an aliquot of solvent (e.g., hydrophilic solvent such as water), then adding the balance of solvent and other materials that are being included in the final consumer product formulation.

It would be appreciated by one of ordinary skill in the art that any of a number of other methods might be used to make compositions comprising the organosiloxane polymer of the present invention. For example, it is not necessary to pre-emulsify the organopolysiloxane conditioning polymer in a separate step but rather it may be emulsify at any point in the making process, as desired. Alternately, it may not be necessary to emulsify the organosiloxane polymer at all, depending upon whether the polymer is soluble in the composition's carrier. Alternately, if the carrier is a solid or semi-solid the organosiloxane conditioning polymer might be directly applied to the carrier.

Similarly, the compositions comprising the roganopolysiloxane conditioning polymer might include any of a number of ingredients including any of the non-limiting ingredients and/or ingredient types discussed herein. Details of the incorporation of said optional ingredients are known to one of skill in the art and the cleaning and/or treatment compositions of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303 all of which are incorporated herein by reference.

VII. Methods of Use

Certain of the consumer products disclosed herein can be used to clean or treat a substrates inter alia a substrate or fabric including physiological substrates and non-physiological substrates. Typically at least a portion of the substrates is contacted with an embodiment of Applicants' composition, in neat form or diluted in a liquor, for example, a wash liquor and then the substrates may be optionally washed and/or rinsed. In one aspect, a substrates is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the substrates comprises a fabric, the water to fabric ratio is typically from about 1:1 to about 30:1.

EXAMPLES

The following examples further describe and demonstrate exemplary embodiments within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

Examples of Organopolysiloxane Conditioning Polymers:

Examples 1-38 of Table 1 list non-limiting examples of the organopolysiloxane conditioning polymers of the present invention and their charge densities. In the examples of Table 1 below:

$w=2$ $y=z=0$ $R_1$ and $R_2$=methyl $X$=propylene $n=2$

TABLE 1

| Ex. No. | x | $R_3$ | E | E' | m | $A^{-t}$ | k | Average Charge Density (meq/g of polymer) |
|---|---|---|---|---|---|---|---|---|
| 1 | 40 | NA | hexylene | hexylene | 2 | Br$^-$ | 3 | 1.57 |
| 2 | 40 | NA | hexylene | hexylene | 4 | Br$^-$ | 5 | 2.14 |
| 3 | 40 | NA | hexylene | hexylene | 10 | Br$^-$ | 11 | 3.07 |
| 4 | 40 | NA | hexylene | hexylene | 20 | Br$^-$ | 21 | 3.71 |
| 5 | 400 | aminopropyl | hexylene | hexylene | 0.25* | Br$^-$ | 3 | 0.097 |
| 6 | 400 | aminopropyl | hexylene | hexylene | 0.5* | Br$^-$ | 3 | 0.128 |
| 7 | 400 | NA | hexylene | hexylene | 2 | Br$^-$ | 3 | 0.19 |
| 8 | 400 | NA | hexylene | hexylene | 5 | Br$^-$ | 6 | 0.37 |
| 9 | 400 | NA | hexylene | hexylene | 10 | Br$^-$ | 11 | 0.64 |
| 10 | 400 | NA | hexylene | hexylene | 20 | Br$^-$ | 22 | 1.10 |
| 11 | 680 | NA | hexylene | hexylene | 2 | Br$^-$ | 3 | 0.12 |
| 12 | 680 | NA | hexylene | hexylene | 5 | Br$^-$ | 6 | 0.23 |
| 13 | 680 | NA | hexylene | hexylene | 10 | Br$^-$ | 11 | 0.41 |

TABLE 1-continued

| Ex. No. | x | $R_3$ | E | E' | m | $A^{-t}$ | k | Average Charge Density (meq/g of polymer) |
|---|---|---|---|---|---|---|---|---|
| 14 | 400 | NA | dodecylene | ethylene | 2 | Br⁻ | 3 | 0.20 |
| 15 | 400 | aminopropyl | butylene | ethylene | 0.5* | Br⁻ | 3 | 0.128 |
| 16 | 400 | NA | hexylene | hexylene | 20 | Cl⁻ | 21 | 1.10 |
| 17 | 400 | aminopropyl | hexylene | hexylene | 0.5* | Cl⁻ | 3 | 0.128 |
| 18 | 40 | NA | butenylene | hexylene | 10 | Cl⁻ | 11 | 3.69 |
| 19 | 40 | NA | butenylene | hexylene | 20 | Cl⁻ | 21 | 4.70 |
| 20 | 400 | NA | butenylene | hexylene | 2 | Cl⁻ | 3 | 0.20 |
| 21 | 400 | NA | butenylene | hexylene | 5 | Cl⁻ | 6 | 0.38 |
| 22 | 400 | NA | butenylene | ethylene | 2 | Cl⁻ | 3 | 0.19 |
| 23 | 400 | NA | butenylene | ethylene | 10 | Cl⁻ | 11 | 0.63 |
| 24 | 400 | NA | p-xylylene | hexylene | 2 | Cl⁻ | 2 | 0.20 |
| 25 | 400 | NA | p-xylylene | hexylene | 5 | Cl⁻ | 6 | 0.38 |
| 26 | 400 | NA | p-xylylene | ethylene | 2 | Cl⁻ | 3 | 0.20 |
| 27 | 400 | NA | p-xylylene | ethylene | 10 | Cl⁻ | 11 | 0.67 |
| 28 | 400 | NA | hexylene | hexylene | 4 | Br⁻ | 5 | 0.32 |
| 29 | 680 | NA | hexylene | hexylene | 4 | Br⁻ | 5 | 0.19 |
| 30 | 680 | NA | hexylene | hexylene | 20 | Br⁻ | 21 | 0.72 |
| 31 | 400 | NA | p-xylylene | hexylene | 4 | Cl⁻ | 5 | 0.32 |
| 32 | 400 | NA | butenylene | hexylene | 4 | Cl⁻ | 5 | 0.32 |
| 33 | 400 | NA | hexylene | hexylene | 40 | Br⁻ | 41 | 1.76 |
| 34 | 680 | NA | hexylene | hexylene | 40 | Br⁻ | 41 | 1.23 |
| 35 | 335 | NA | hexylene | hexylene | 4 | Br⁻ | 5 | 0.38 |
| 36 | 335 | NA | hexylene | hexylene | 10 | Br⁻ | 11 | 0.75 |
| 37 | 335 | NA | hexylene | hexylene | 20 | Br⁻ | 21 | 1.26 |
| 38 | 335 | NA | hexylene | hexylene | 40 | Br⁻ | 41 | 1.97 |

*When the average m is <1, then not every M group bears a charged group G. In these exemplary cases, the M groups that do not bear the charged group G will carry the group $R_3$ as the propylamino group. Also, in these exemplary cases while the average m may be less than two each individual m for each charged group G may be greater than or equal to two.

Example Silicone Emulsion Compositions

Examples 39-42 of Table 2 list non-limiting examples of emulsions comprising the organopolysiloxane conditioning polymers of the present invention. It would be understood by one of ordinary skill in the art that any of a number of surfactants might be useful in creating the emulsion.s

TABLE 2

| | Example Nos. | | | |
|---|---|---|---|---|
| Ingredients | 39 | 40 | 41 | 42 |
| Organopolysiloxane Polymer of Examples 1-38 | 20 | 20 | 20 | 20 |
| Tergitol 15-S-5[1] | 3.00 | 1.00 | 0.5 | 1.12 |
| Tergitol 15-S-12[2] | — | — | — | 1.88 |
| Acetic Acid[3] | to pH 5 | to pH 5 | to pH 5 | to pH 5 |
| Water | q.s. to 100% | q.s. to 100% | q.s. to 100% | q.s. to 100% |

[1]Available from Sigma Aldrich
[2]Available from Sigma Aldrich
[3]Available from Sigma Aldrich (98% pure)

Example Shampoo Compositions

Examples 43-50 of Table 4 list non-limiting examples of shampoo compositions comprising the organopolysiloxane conditioning polymers of the present invention.

TABLE 3

| Ingredient | Example Nos. | | | | | | | |
|---|---|---|---|---|---|---|---|---|
| | 43 | 44 | 45 | 46 | 47 | 48 | 49 | 50 |
| Water | q.s. to 100% | q.s. to 100% | q.s. to 100% | q.s. to 100% | q.s. to 100% | q.s. to 100% | q.s. to 100% | q.s. to 100% |
| Polyquaternium 76[1] | 0.25 | — | — | — | 0.25 | — | — | — |
| Guar, Hydroxypropyl Trimonium Chloride[2] | — | 0.25 | — | — | — | 0.25 | — | — |
| Polyquaternium 6[3] | — | — | 0.79 | — | — | — | 0.79 | — |
| Sodium Laureth Sulfate (SLE3S)[4] | 21.43 | 21.43 | 21.43 | 21.43 | — | — | — | — |
| Sodium Laureth Sulfate (SLE1S)[4] | — | — | — | — | 10.50 | 10.50 | 10.50 | 10.50 |
| Sodium Lauryl Sulfate (SLS)[5] | 20.69 | 20.69 | 20.69 | 20.69 | 1.5 | 1.5 | 1.5 | 1.5 |
| Emulsion according to any of Examples 39-42 | 5.00 | 5.00 | 5.00 | 5.00 | 5.00 | 5.00 | 5.00 | 5.00 |
| Cocoamidopropyl Betaine[6] | 3.33 | 3.33 | 3.33 | 3.33 | 1.0 | 1.0 | 1.0 | 1.0 |
| Cocoamide MEA[7] | 1.0 | 1.0 | 1.0 | 1.0 | 1.0 | 1.0 | 1.0 | 1.0 |
| Ethylene Glycol Distearate[8] | 1.50 | 1.50 | 1.50 | 1.50 | 1.50 | 1.50 | 1.50 | 1.50 |
| Sodium Chloride[9] | 0.25 | 0.25 | 0.25 | 0.25 | 0.25 | 0.25 | 0.25 | 0.25 |
| Fragrance | 0.70 | 0.70 | 0.70 | 0.70 | 0.70 | 0.70 | 0.70 | 0.70 |

TABLE 3-continued

| Ingredient | 43 | 44 | 45 | 46 | 47 | 48 | 49 | 50 |
|---|---|---|---|---|---|---|---|---|
| Preservatives, pH adjusters | Up to 1% | Up to 1% | Up to 1% | Up to 1% | Up to 1% | Up to 1% | Up to 1% | Up to 1% |

[1] Mirapol ® AT-1, Copolymer of Acrylamide(AM) and TRIQUAT, MW = 1,000,000; CD = 1.6 meq./gram; 10% active; Supplier Rhodia
[2] Jaguar ® C500, MW—500,000, CD = 0.7, supplier Rhodia
[3] Mirapol ® 100S, 31.5% active, supplier Rhodia
[4] Sodium Laureth Sulfate, 28% active, supplier: P&G
[5] Sodium Lauryl Sulfate, 29% active supplier: P&G
[6] Tego ® betaine F-B, 30% active supplier: Goldschmidt Chemicals
[7] Monamid CMA, 85% active, supplier Goldschmidt Chemical
[8] Ethylene Glycol Distearate, EGDS Pure, supplier Goldschmidt Chemical
[9] Sodium Chloride USP (food grade), supplier Morton; note that salt is an adjustable ingredient, higher or lower levels may be added to achieve target viscosity Examples 51-55 of Table 4 list additional non-limiting examples of shampoo compositions comprising the organopolysiloxane conditioning polymers of the present invention.

Example Hair Conditioner Compositions

Examples 55-57 of Table 5 list non-limiting examples of hair conditioner compositions comprising the organopolysiloxane conditioning polymers of the present invention.

TABLE 4

| Ingredient | 51 | 52 | 53 | 54 | 55 |
|---|---|---|---|---|---|
| Water | q.s. to 100% | q.s. to 100% | q.s. to 100% | q.s. to 100% | q.s. to 100% |
| Emulsion according to any of Examples 39-42 | 2 | 2 | 4 | 4 | 10 |
| Polyquaterium 76 [1] | 0.25 | | | | 0.1 |
| Polquaterium 10 [2] | | 0.25 | 0.25 | | |
| Polyquaterium 6 [3] | | | | 0.1 | |
| Guar Hydroxpropyltrimonium Chloride [4] | | | | | 0.2 |
| Sodium Laureth Sulfate (SLE3S - 28% active) [5] | 21.43 | 35.71 | 35.71 | | |
| Sodium Laureth Sulfate (SLE1S - 29% active) [6] | | | | 44.83 | 37.93 |
| Sodium Lauryl Sulfate (SLS - 29% active) [7] | 12.07 | 24.14 | 24.14 | — | — |
| Coco monoethanolamide [8] | 1.0 | 0.5 | 0.5 | — | — |
| Cocoamdopropyl Betaine (30% active) [9] | 2.5 | — | — | 3.33 | 5.0 |
| Ethylene Glycol Disterate [10] | — | 1.5 | 1.5 | — | — |
| 330M silicone [11] | 1.43 | 1.43 | 1.43 | — | — |
| Silicone microemulsion [12] | — | — | — | — | 4 |
| Trihydroxystearn [13] | 0.25 | — | 0.25 | 0.25 | 0.25 |
| Sodium Chloride [14] | Adjust as needed for viscosity | Adjust as needed for viscosity | Adjust as needed for viscosity | Adjust as needed for viscosity | Adjust as needed for viscosity |
| Fragrance | 0.7 | 0.7 | 0.7 | 0.7 | 0.7 |
| Preservatives, pH adjusters | Up to 1% | Up to 1% | Up to 1% | Up to 1% | Up to 1% |

[1] Acrylamide:Triquat cationic polymer, tradname: Mirapol AT from Rhodia,
[2] KG30M cationic cellulose polymer from Amerchol Dow
[3] Polydadmac, tradename: Mirapol 100S from Rhodia
[4] Jaguar C500 from Rhodia
[5] Sodium Laureth (3 molar ethylene oxide) Sulfate at 28% active, supplier: P&G
[6] Sodium Laureth (1 molar ethylene oxide) sulfate at 29% active, supplier: P&G
[7] Sodium Lauryl Sulfate at 29% active, supplier: P&G
[8] Coco monethanolamide at 85% active, supplier: Stephan Co
[9] Tegobetaine F-B, 30% active, supplier: Goldschmidt Chemical
[10] Ethylene Glycol Disterate at 100% active, supplier: Goldschmidt Chemical
[11] 330M silicone, 100% active, supplier: Momentive (silicone used by P&G to make a 70% active, 30 um emulsion)
[12] Belsil 3560 VP silicone microemulsion from Wacker, 60,000 cst internal viscosity of silicone, approx. 125 nm
[13] Thixin R from Rheox Inc.
[14] Sodium Chloride USP (food grade) from Morton

TABLE 5

| Ingredients | Example Nos. | | |
|---|---|---|---|
| | 55 | 56 | 57 |
| Water | q.s. to 100% | q.s. to 100% | q.s. to 100% |
| Emulsion according to any of Examples 39-42 | 5.00 | 5.00 | 5.00 |
| Behentrimonium methosulfate/IP [1] | 2.37 | 3.45 | — |
| Stearamidopropyl Dimethylamine [2] | — | — | 1.19 |
| Cetyl alcohol [3] | 1.15 | 1.07 | 1.73 |
| Stearyl alcohol [4] | 2.88 | 2.66 | 3.19 |
| Disodium EDTA | 0.13 | 0.13 | 0.14 |
| Benzyl alcohol | 0.41 | 0.40 | 0.45 |
| Methylchloroisothiazolinone/Methylisothiazolinone [5] | 0.03 | 0.03 | 0.04 |
| Panthenol [6] | — | 0.05 | — |
| Panthenyl ethyl ether [7] | — | 0.03 | — |
| Fragrance | 0.51 | 0.50 | — |
| Dicetyldimonium Chloride in Propylene Glycol | — | — | 0.57 |
| L-Gutamic Acid | — | — | 0.38 |
| Citric Acid Anhydrous | — | — | 0.06 |

[1] Behentrimonium methosulfate/Isopropyl alcohol: Genamin BTMS available from Clariant
[2] Stearamidopropyl Dimethylamine: Available from Croda Inc.
[3] Cetyl alcohol: Konol TM series available from Shin Nihon Rika
[4] Stearyl alcohol: Konol TM series available from Shin Nihon Rika
[5] Methylchloroisothiazolinone/Methylisothiazolinone: Kathon TM CG available from Rohm & Haas
[6] Panthenol: Available from Roche
[7] Panthenyl ethyl ether: Available from Roche Examples 58 of Table 6 lists an additional non-limiting example of a hair conditioner compositions comprising the organopolysiloxane conditioning polymers of the present invention.

TABLE 6

| Ingredients | Example No. 58 |
|---|---|
| Emulsion according to any of Examples 39-42 | 3.00 |
| Cetyltrimethyl ammonium chloride | 1.00 |
| Polymethylphenyl siloxane [1] | 1.00 |
| Phenoxy ethanol | 0.40 |
| PHB-methylester | 0.20 |
| Copolymer of aminoethyl aminopropyl siloxane and dimethyl siloxane [2] | 1.00 |
| Isododecane | 5.00 |
| Perfume oil | 0.40 |
| Water | q.s. to 100% |

[1] Available as Abil Quat 3272
[2] Available as Dow Corning 949 Cationic Emulsion Example Leave-on Hair Conditioner Compositions Examples 59-64 of Tables 7-9 list non-limiting examples of leave-on hair conditioner compositions comprising the organopolysiloxane conditioning polymers of the present invention.

TABLE 7

| Ingredients | Example No. 59 |
|---|---|
| Emulsion according to any of Examples 39-42 | 1.00 |
| 2-hydroxy-3-(trimethylamonio)propylether chloride guar gum | 0.50 |
| Sodium benzoate | 0.50 |
| Glyoxylic acid | 0.10 |
| Creatine | 0.20 |
| Behenyl trimethylammonium chloride | 0.80 |
| Cetylstearyl alcohol | 0.60 |
| Stearic acid polyethylenglycol (20 EO) | 0.10 |
| Hydrolyzed silk | 0.10 |
| Perfume oil | 0.20 |
| Water | q.s. to 100% |

TABLE 8

| Ingredients | Example No. 60 |
|---|---|
| Emulsion according to any of Examples 39-42 | 1.80 |
| Vitamine E-acetate | 0.10 |
| Polymethylphenyl siloxane [1] | 0.50 |
| Propylenelycol | 10.00 |
| Behenyl trimethylammonium chloride | 0.50 |
| Sodium chloride | 0.05 |
| D-panthenol | 0.30 |
| PHB-propylester | 0.30 |
| Isododecane | 2.00 |
| Perfume oil | 0.20 |
| Water | q.s. to 100% |

[1] Quaternium-80, available as Abil Quat(R) 3272

TABLE 9

| Ingredients | Example Nos. | | | |
|---|---|---|---|---|
| | 61 | 62 | 63 | 64 |
| Emulsion according to any of Examples 39-42 | 3.50 | | | |
| Organopolysiloxane according to any of Examples 1-38 | | 2.00 | 5 | 10 |
| Vitamine E-acetate | 0.10 | | | |
| Polymethylphenyl siloxane [1] | 0.50 | | | |
| Cyclopentasiloxane | 21.00 | | | |
| Dihydroxy polydimethyl siloxane | 2.50 | | | |
| Ethanol | 1.50 | 93.00 | 94.50 | 89.50 |
| Perfume oil | 0.60 | 0.50 | 0.50 | 0.50 |
| Water | q.s. to 100% | q.s. to 100% | q.s. to 100% | q.s. to 100% |

[1] Quaternium-80, available as Abil Quat(R) 3272

Example Liquid Fabric Detergent Compositions

Examples 65-68 of Table 10 list non-limiting examples of liquid fabric detergent compositions comprising the organopolysiloxane conditioning polymers of the present invention.

TABLE 10

| Ingredients | Example Nos. | | | |
|---|---|---|---|---|
| | 65 | 66 | 67 | 68 |
| C12-C15 alkyl polyethoxylate (1.8) sulfate[1] | 26.83 | 14.81 | — | 10.70 |
| C11.8 linear alkylbenzene sulfonc acid[2] | 4.19 | 3.53 | 10.70 | — |
| C12 alkyl dimethyl amine oxide[3] | 1.69 | 0.56 | — | — |
| C12-C14 alcohol 9 ethoxylate[4] | — | 0.78 | 10.70 | 10.70 |
| 1,2 Propane diol | — | 3.47 | 3.47 | 3.47 |
| Ethanol | — | 2.79 | 2.79 | 2.79 |
| C12-C18 Fatty Acid[5] | 1.42 | 1.48 | 1.48 | 1.48 |

TABLE 10-continued

| Ingredients | 65 | 66 | 67 | 68 |
|---|---|---|---|---|
| Citric acid[6] | 5.34 | 2.05 | 2.05 | 2.05 |
| Emulsion according to any of Examples 39-42 | 20.00 | 20.00 | 20.00 | 20.00 |
| Water, perfumes, dyes, buffers, enzymes, solvents and other optional components | q.s. to 100% pH 8.0-8.2 | q.s. to 100% pH 8.0-8.2 | q.s. to 100% pH 8.0-8.2 | q.s. to 100% pH 8.0-8.2 |

[1]Available from Shell Chemicals, Houston, TX.
[2]Available from Huntsman Chemicals, Salt Lake City, UT.
[3]Available from The Procter &amble Company, Cincinnati, OH.
[4]Available from Sasol Chemicals, Johannesburg, South Africa
[5]Available from The Procter &amble Company, Cincinnati, OH.
[6]Available from Enencor International, South San Francisco, CA.

Examples 69-70 of Table 11 exemplify additional non-limiting examples of liquid fabric detergent compositions comprising the organopolysiloxane conditioning polymers of the present invention.

TABLE 11

| Ingredients | 69 | 70 |
|---|---|---|
| C24 alkyl polyethoxylate (3.0) sulfate[1] | 6.8 | 6.8 |
| C11.8 linear alkylbenzene sulfonic acid[2] | 3.1 | 3.1 |
| C24 alkyl 7-ethoxylate[1] | 0.93 | 0.93 |
| C45 alkyl 7-ethoxylate[3] | 2.80 | 2.80 |
| 1,2 Propane diol | 4.58 | 4.58 |
| Ethanol | 0.86 | 0.86 |
| Di Ethylenelycol | — | — |
| Na Cumene Sulfonate | — | — |
| C12-C18 Fatty Acid | 4.1 | 4.1 |
| Citric acid | 3.2 | 3.2 |
| Protease (40.6 mg/g/) | 0.021 | 0.021 |
| Natalase 200L (29.26 mg/g) | 0.003 | 0.003 |
| Termamyl Ultra (25.1 mg/g) | 0.001 | 0.001 |
| Emulsion according to any of Examples 39-42 | 3 | 5 |
| Water, perfumes, dyes, buffers, neutralizers, stabilizers and other optional components | q.s. to 100% pH 8.0-8.2 | q.s. to 100% pH 8.0-8.2 |

[1]Available from Shell Chemicals, Houston, TX.
[2]Available from Huntsman Chemicals, Salt Lake City, UT.
[3]Available from Sasol Chemicals, Johannesburg, South Africa Examples 71-75 of Table 12 list additional non-limiting examples of liquid fabric detergent compositions comprising the organopolysiloxane conditioning polymers of the present invention

TABLE 12

| Ingredients | 71 | 72 | 73 | 74 | 75 |
|---|---|---|---|---|---|
| Sodium alkyl ether sulfate | 20.5 | 20.5 | 20.5 | | |
| C12-15 Alkyl Polyethoxylate (1.1) Sulfonic Acid | | | | 9.0 | |
| Branched alcohol sulfate | 5.8 | 5.8 | 5.8 | | |
| Linear alkylbenzene sulfonic acid | 2.5 | 2.5 | 2.5 | 1.0 | 8.0 |
| Alkyl ethoxylate | 0.8 | 0.8 | 0.8 | 1.5 | 6.0 |
| Amine oxide | 0 | 0.5 | 2 | | 1.0 |
| Citric acid | 3.5 | 3.5 | 3.5 | 2.0 | 2.5 |
| Fatty acid | 2.0 | 2.0 | 2.0 | | 5.5 |
| Protease | 0.7 | 0.7 | 0.7 | 0.4 | 0.4 |
| Amylase | 0.37 | 0.37 | 0.37 | 0.08 | 0.08 |
| Mannanase | | | | 0.03 | 0.03 |
| Borax (38%) | 3.0 | 3.0 | 3.0 | 1.0 | |
| MEA Borate | | | | | 1.5 |
| Calcium and sodium formate | 0.22 | 0.22 | 0.22 | 0.7 | |
| Amine ethoxylate polymers | 1.2 | 0.5 | 1.0 | 1.0 | 1.5 |
| Zwitterionic amine ethoxylate polymer | 1.0 | 2.0 | 1.0 | | |
| Emulsion according to any of Examples 39-42 | 0.5 | 1.0 | 2.0 | 1.0 | 5.0 |
| DTPA[1] | 0.25 | 0.25 | 0.25 | 0.3 | 0.3 |
| Fluorescent whitening agent | 0.2 | 0.2 | 0.2 | | |
| Ethanol | 2.9 | 2.9 | 2.9 | 1.5 | 1.5 |
| Propylenelycol | | | | 3.0 | 5.0 |
| Propanediol | 5.0 | 5.0 | 5.0 | | |
| Diethylenelycol | 2.56 | 2.56 | 2.56 | | |
| Polyethylenelycol 4000 | 0.11 | 0.11 | 0.11 | | |
| Monoethanolamine | 2.7 | 2.7 | 2.7 | 1.0 | 0.5 |
| Sodium hydroxide (50%) | 3.67 | 3.67 | 3.67 | 1.4 | 1.4 |
| Sodium cumene sulfonate | 0 | 0.5 | 1 | | 0.7 |
| Silicone suds suppressor | 0.01 | 0.01 | 0.01 | | 0.02 |
| Perfume | 0.5 | 0.5 | 0.5 | 0.30 | 0.3 |
| Dye | 0.01 | 0.01 | 0.01 | 0.016 | 0.016 |
| Opacifier[2] | 0.01 | 0.01 | 0.01 | | |
| Water | q.s. to 100% | q.s. to 100% | q.s. to 100% | q.s. to 100% | q.s. to 100% |

[1]Diethylenetriaminepentaacetic acid, sodium salt
[2]Acusol OP 301

Example Granular Laundry Detergent Compositions

Examples 76-79 of Table 13 list non-limiting examples of granular fabric detergent compositions comprising the organopolysiloxane conditioning polymers of the present invention.

TABLE 13

| Ingredients | 76 | 77 | 78 | 79 |
|---|---|---|---|---|
| Emulsion according to any of Examples 39-42 | 0.5 | 2.5 | 5.0 | 10 |
| Sodium alkylbenzenesulfonate | 16.0000 | 14.0000 | 12.0000 | 7.9 |
| Sodium alkyl alcohol ethoxylate (3) sulfate | — | — | — | 4.73 |
| Sodium mid-cut alkyl sulfate | | 1.5000 | 1.5000 | — |
| Alkyl dimethyl hydroxyethyl quaternary amine (chloride) | — | — | — | 0.5 |
| Alkyl ethoxylate | 1.3000 | 1.3000 | 1.3000 | — |
| Polyamine[1] | — | — | — | 0.79 |
| Nonionic Polymer[2] | 1.0000 | 1.0000 | 1.0000 | 1.0 |
| Carboxymethylcellulose | 0.2000 | 0.2000 | 0.2000 | 1.0 |
| Sodium polyacrylate | — | — | — | — |
| Sodium polyacrylate/maleate polymer | 0.7000 | 0.7000 | 0.7000 | 3.5 |
| Sodium tripolyphosphate | 10.0000 | 5.0000 | — | — |
| Zeolite | 16.0000 | 16.0000 | 16.0000 | — |
| Citric Acid | — | — | — | 5.0 |
| Sodium Carbonate | 12.5000 | 12.5000 | 12.5000 | 25.0 |
| Sodium Silicate | 4.0 | 4.0 | 4.0 | — |
| Enzymes[3] | 0.30 | 0.30 | 0.30 | 0.5 |

TABLE 13-continued

|  | Example Nos. | | | |
|---|---|---|---|---|
| Ingredients | 76 | 77 | 78 | 79 |
| Minors including moisture[4] | q.s. to 100% | q.s. to 100% | q.s. to 100% | q.s. to 100% |

[1]Hexamethylenediamine ethoxylated to 24 units for each hydrogen atom bonded to a nitrogen, quaternized.
[2]Comb polymer of polyethylenelycol and polyvinylacetate
[3]Enzyme cocktail selected from known detergent enzymes including amylase, cellulase, protease, and lipase.
[4]Balance to 100% can, for example, include minors like optical brightener, perfume, suds suppresser, soil dispersant, soil release polymer, chelating agents, bleach additives and boosters, dye transfer inhibiting agents, aesthetic enhancers (example: Speckles), additional water, and fillers, including sulfate, CaCO3, talc, silicates, etc.

Example Unit Dose Laundry Detergent Compositions

Example 80 of Table 14 lists a non-limiting examples of unit-dose fabric detergent compositions comprising the organopolysiloxane conditioning polymers of the present invention.

TABLE 14

| Ingredients | Example No. 80 |
|---|---|
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| Nonionic Marlipal C24EO7 | 20.1 |
| HLAS | 24.6 |
| Optical brightener FWA49 | 0.2 |
| Emulsion according to any of Examples 39-42 | 0.5-15 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Enzymes | ppm |

Example Fabric Treatment Compositions

Examples 81-84 of Table 15 lists non-limiting examples of fabric treatment compositions comprising the organopolysiloxane conditioning polymers of the present invention.

TABLE 15

|  | Example Nos. | | | |
|---|---|---|---|---|
| Ingredients | 81 | 82 | 83 | 84 |
| Fabric Softener Active[1] | 16.0 | 11.0 | 16.2 | — |
| Fabric Softener Active[2] | — | — | — | 5.0 |
| Cationic Starch[3] | 1.5 | — | 1.5 | — |
| Polyethylene imine[4] | 0.25 | — | — | — |
| Quaternized polyacrylamide[5] | — | 0.2 | 0.25 | 0.25 |
| Calcium chloride | 0.15 | 0.15 | 0.15 | — |
| Ammonium chloride | 0.1 | 0.1 | 0.1 | — |
| Suds Suppressor[6] | — | — | — | 0.1 |
| Emulsion according to any of Examples 39-42 | 10.0 | 15.0 | 10.0 | 15.0 |
| Perfume | 0.85 | 2.0 | 0.85 | 1.0 |
| Perfume microcapsule[7] | 0.65 | 0.75 | 0.65 | 0.3 |
| Water, suds suppressor, stabilizers, pH control agents, buffers, dyes & other optional ingredients | q.s. to 100% pH = 3.0 | q.s. to 100% pH = 3.0 | q.s. to 100% pH = 3.0 | q.s. to 100% pH = 3.0 |

[1]N,N di(tallowoyloxyethyl) - N,N dimethylammonium chloride available from Evonik Corporation, Hopewell, VA.
[2]Reaction product of fatty acid with Methyldiethanolamine, quaternized with Methylchloride, resulting in a 2.5:1 molar mixture of N,N-di(tallowoyloxyethyl) N,N-dimethylammonium chloride and N-(tallowoyloxyethyl) N-hydroxyethyl N,N-dimethylammonium chloride available from Evonik Corporation, Hopewell, VA.
[3]Cationic starch based on common maize starch or potato starch, containing 25% to 95% amylose and a degree of substitution of from 0.02 to 0.09, and having a viscosity measured as Water Fluidity having a value from 50 to 84. Available from National Starch, Bridgewater, NJ
[4]Available from Nippon Shokubai Company, Tokyo, Japan under the trade name Epomin 1050.
[5]Cationic polyacrylamide polymer such as a copolymer of acrylamide/[2-(acryloylamino) ethyl]trimethylammonium chloride (quaternized dimethyl aminoethyl acrylate) available from BASF, AG, Ludwigshafen under the trade name Sedipur 544.
[6]SILFOAM ® SE90 available from Wacker AG of Munich, ermany
[7]Available from Appleton Paper of Appleton, WI Examples 85-93 of Table 16 list additional non-limiting examples of fabric treatment compositions comprising the organopolysiloxane conditioning polymers of the present invention.

TABLE 16

|  | Example Nos. | | | | | | | | |
|---|---|---|---|---|---|---|---|---|---|
| Ingredients | 85 | 86 | 87 | 88 | 89 | 90 | 91 | 92 | 93 |
| Emulsion according to any of Examples 39-4 | 6.00 | 6.00 | 6.00 | 6.00 | 6.00 | 12.00 | 12.00 | 12.00 | 12.00 |
| Cationic starch[1] | 1.20 | 1.20 | 1.20 | 1.20 | 1.20 | 1.20 | 1.20 | 1.20 | 1.20 |
| Tae80[2] | 0.25 | 0.25 | 0.25 | 0.25 | 0.25 | 0.25 | 0.25 | 0.25 | 0.25 |
| Antimicrobial | 0.02 | 0.02 | 0.02 | 0.02 | 0.02 | 0.02 | 0.02 | 0.02 | 0.02 |
| Perfume | 0.40 | 0.40 | 0.40 | 0.40 | 0.40 | 0.40 | 0.40 | 0.40 | 0.40 |
| Butyl carbitol | 3.00 | 3.00 | 3.00 | 3.00 | 3.00 | 2.00 | 2.00 | 2.00 | 2.00 |
| Polyamine N-oxide | 0.00 | 0.83 | 1.67 | 3.34 | 5.00 | 0.00 | 1.67 | 3.34 | 5.00 |
| Water | q.s. to 100% | q.s. to 100% | q.s. to 100% | q.s. to 100% | q.s. to 100% | q.s. to 100% | q.s. to 100% | q.s. to 100% | q.s. to 100% |

[1]Akzo, EXP 5617-2301-28, available from Akzo Nobel.
[2]Tallow alkyl ethoxylated alcohol having an average degree of ethoxylation of 80.

Test Results for Shampoos

Table 17 lists non-limiting examples of shampoo compositions that are evaluated for their ability to reduce hair-friction. Hair friction is evaluated per the Texture Analyzer method outlined below. Data from these evaluations are given in Table 18 below.

TABLE 17

| SHAMPOO FORMULATION | Example Nos. | |
|---|---|---|
| | 94 | 95 |
| Water | q.s. to 100% | q.s. to 100% |
| Guar, Hydroxypropyl Trimonium Chloride [1] | 0.25 | 0.25 |
| Sodium Laureth Sulfate (SLE1S) [2] | 10.50 | 10.50 |
| Sodium Lauryl Sulfate (SLS) [3] | 1.5 | 1.5 |
| Emulsion according to Example 39[4] | 5.00 | — |
| Cocoamidopropyl Betaine [5] | 1.0 | 1.0 |
| Cocoamide MEA [6] | 1.0 | 1.0 |
| Ethylenelycol Distearate [7] | 1.50 | 1.50 |
| Sodium Chloride [8] | 0.25 | 0.25 |
| Fragrance | 0.70 | 0.70 |
| Preservatives, pH adjusters | Up to 1% | Up to 1% |

[1] Jaguar ® C500, MW - 500,000, CD = 0.7, supplier Rhodia
[2] Sodium Laureth Sulfate, 28% active, supplier: P&G
[3] Sodium Lauryl Sulfate, 29% active supplier: P&G
[4] Comprising organopolysiloxane conditioning polymer of Examples 9, 10, 13, 28, 29, 30
[5] Tego ® betaine F-B, 30% active supplier: oldschmidt Chemicals
[6] Monamid CMA, 85% active, supplieroldschmidt Chemical
[7] Ethylenelycol Distearate, EGDS Pure, supplieroldschmidt Chemical
[8] Sodium Chloride USP (foodrade), supplier Morton; note that salt is an adjustable ingredient, higher or lower levels may be added to achieve target viscosity Hair Treatment Method An automated brush protocol is used to treat moderetly damaged hair purchased from International Hair Importer & Products Inc. In this automated treatment process, the shampoo formulation is added to pre-wetted hair switches manually. The shampoo is applied in a zig-zag form at 0.05 g of product/g of hair. A set of brushes will spread the product to the entire hair by brushing up and down for 30 seconds followed by a brush rinse for an additional 30 seconds. The rinse water is run at 6.5 gallons per minute at a temperature of 100° F. This process is repeated 3 times to complete a 3 cycle treatment. A separate rinsing process is followed after completing the 3 cycle treatment using an automated rinse tester. During this process, hair switches are rinsed using city tap water sprayed through two nozzles at a flow rate between 200 to 500 ml/min. A clamping device compresses the hair switches between two pads that squeeze the water out while sliding down the hair switch. After sliding the pad down the hair 21 times (21 strokes), the hair switch is removed and let air dry in a humidity controlled room.

The hair feel is measured using a texture analyzer test to measure the hair to hair interaction (resistance/friction) while applying a constant pressure of 1400 f to a hair switch, sandwiched between artificial skin surrogates. The instrument uses a probe that when pressurized, pinches the hair against a flat surface then cycles up and down for five complete strokes. Both sides of the switch are to be evaluated to determine the consistency of the treatment. Pantene Smooth and Sleek is a 2-in-1 commercially available cosmetic shampoo with 1.35% PDMS was used as a reference control in the test. The Pantene Smooth and Sleek reference control should give a result of about 1855 gF (gram force)+ 10% RSD (relative standard deviation) in this test. The shampoo according to Example 95 provides an experimental control as a composition that does not comprise the organopolysiloxane of the present invention.

TABLE 18

| Shampoo | Average Peak Sum Dry Friction (gF) |
|---|---|
| Shampoo according to Example 94 comprising the organopolysiloxane of Example 29 | 1197 |
| Shampoo according to Example 94 comprising the organopolysiloxane of Example 30 | 1355 |
| Shampoo according to Example 94 comprising the organopolysiloxane of Example 10 | 1387 |
| Shampoo according to Example 94 comprising the organopolysiloxane of Example 9 | 1451 |
| Shampoo according to Example 94 comprising the organopolysiloxane of Example 28 | 1490 |
| Shampoo according to Example 94 comprising the organopolysiloxane of Example 13 | 1548 |
| Shampoo according to Example 95 | 2927 |
| Pantene smooth and sleek with PDMS | 1958 |

Test Results for Hair Conditioners

Table 19 lists non-limiting examples of hair-conditioner compositions that are evaluated for their ability to reduce hair-friction. Hair friction is evaluated per the Instron Friction Method outlined below. Data from these evaluations are given in Tables 20-22.

TABLE 19

| Ingredients | Example Nos. | | | | | |
|---|---|---|---|---|---|---|
| | 96 | 97 | 98 | 99 | 100 | 101 |
| Water | to 100% | to 100% | to 100% | to 100% | to 100% | to 100% |
| Emulsion according to Example 39[1] | 5.00 | — | — | — | — | — |
| Emulsion according to Example 40[2] | — | 5.00 | — | — | — | — |
| Emulsion according to Example 41[2] | — | — | 5.00 | — | — | — |
| Behentrimonium methosulfate/IP[3] | 2.37 | 3.45 | — | 2.37 | 3.45 | — |
| Stearamidopropyl Dimethylamine | — | — | — | — | — | — |
| Cetyl alcohol[4] | 1.15 | 1.07 | 1.73 | 1.15 | 1.07 | 1.73 |
| Stearyl alcohol[5] | 2.88 | 2.66 | 3.19 | 2.88 | 2.66 | 3.19 |
| Disodium EDTA | 0.13 | 0.13 | 0.14 | 0.13 | 0.13 | 0.14 |
| Benzyl alcohol | 0.41 | 0.40 | 0.45 | 0.41 | 0.40 | 0.45 |
| Methylchloroisothiazolinone/Methylisothiazolinone[6] | 0.03 | 0.03 | 0.04 | 0.03 | 0.03 | 0.04 |
| Panthenol[7] | — | 0.05 | — | — | 0.05 | — |
| Panthenyl ethyl ether[8] | — | 0.03 | — | — | 0.03 | — |

TABLE 19-continued

| Ingredients | Example Nos. | | | | | |
|---|---|---|---|---|---|---|
| | 96 | 97 | 98 | 99 | 100 | 101 |
| Fragrance | 0.51 | 0.50 | — | 0.51 | 0.50 | — |
| Dicetyldimonium Chloride in Propylenelycol | — | — | 0.57 | — | — | 0.57 |
| L-Gutamic Acid | — | — | 0.38 | — | — | 0.38 |
| Citric Acid Anhydrous | — | — | 0.06 | — | — | 0.06 |

[1]Comprising organopolysiloxane conditioning polymers of Examples 9, 10, 13, 23, 27, 28, 30-34
[2]Comprising organopolysiloxane conditioning polymers of Example 28
[3]Behentrimonium methosulfate/Isopropyl alcohol: enamin BTMS available from Clariant
[4]Cetyl alcohol: Konol TM series available from Shin Nihon Rika
[5]Stearyl alcohol: Konol TM series available from Shin Nihon Rika
[6]Methylchloroisothiazolinone/Methylisothiazolinone: Kathon TM CG available from Rohm & Haas
[7]Panthenol: Available from Roche
[8]Panthenyl ethyl ether: Available from Roche For conditioner testing, 20 g of moderately damaged hair purchased from International Hair Importer & Products Inc is system treated with 1 mL of shampoo (0.05 g of shampoo/of hair) is treated by a milking process. The switch is lathered with milking motion for 30 secs and rinsed 15 seconds on each side. The shampoo application and lathering is repeated, ending with a 120 second rinse (60 secs on each side). The shampoo used in this system test was Pantene Medium-Thick Frizzy to Smooth. After the shampoo application, 2.0 mL of conditioner is applied followed by a 30 second rinse. Finally, the switch is squeezed, pat-towel-dried, combed and hung to dry in 21° C./45% RH room for at least 18 hours. An instron friction measurement (IFM) is used to evaluate the dry hair smoothness. Dried hair is clipped on the right side of the friction table and combed with narrow teeth side of comb 2 times to haveood hair alignment. A 200 g sled-weight is put on the middle of the hair switch and slide down without disrupting the hair alignment. The bottom of the sled is prepared by attaching a piece of polyurethane that exactly fits the bottom of the sled including edges. Measurement is performed five times per treatment and the force to slide the 200 g sled is recorded and average. In conditioners, MF100, M10P1, are used as reference controls in the test. The MF100 and M10P1 references control should give a result between 100 gF and 155 gF and between 124 and 187 respectively, in this test. Examples 99, 100, and 101 serve as experimental controls for examples 96, 97 and 98, respectively. M10P1 is a conditioner with a 4.2% blend of 18MMcst PDMSum with D5 at 85/15 ratio. MF100 is a conditioner with a 10% blend of 18MMcst PDMSum with 200 cst at 85/15 ratio.

TABLE 20

| Conditioner | Friction (gF) |
|---|---|
| Conditioner according to Example 96 comprising the organopolysiloxane conditioning polymer of Example 33 | 78 |
| Conditioner according to Example 96 comprising the organopolysiloxane conditioning polymer of Example 28 | 80 |
| Conditioner according to Example 96 comprising the organopolysiloxane conditioning polymer of Example 10 | 80 |
| Conditioner according to Example 96 comprising the organopolysiloxane conditioning polymer of Example 9 | 84 |
| Conditioner according to Example 96 comprising the organopolysiloxane conditioning polymer of Example 30 | 93 |
| Conditioner according to Example 96 comprising the organopolysiloxane conditioning polymer of Example 13 | 95 |
| Conditioner according to Example 96 comprising the organopolysiloxane conditioning polymer of Example 34 | 109 |
| Conditioner according to Example 96 comprising the organopolysiloxane conditioning polymer of Example 27 | 91 |
| Conditioner according to Example 96 comprising the organopolysiloxane conditioning polymer of Example 31 | 105 |
| Conditioner according to Example 96 comprising the organopolysiloxane conditioning polymer of Example 32 | 107 |
| Conditioner according to Example 96 comprising the organopolysiloxane conditioning polymer of Example 23 | 116 |
| Conditioner according to Example 99 | 179 |
| MF100 | 107 |
| M10P1 | 159 |

TABLE 21

| Conditioner | Friction (gF) |
|---|---|
| Conditioner according to Example 97 comprising the organopolysiloxane conditioning polymer of Example 28 | 107 |
| Conditioner according to Example 100 | 160 |
| MF100 | 133 |
| M10P1 | 166 |

TABLE 22

| Conditioner | Friction (gF) |
|---|---|
| Conditioner according to Example 98 comprising the organopolysiloxane conditioning polymer of Example 28 | 97 |
| Conditioner according to Example 101 | 179 |
| MF100 | 131 |
| M10P1 | 185 |

Energy Extraction Results—Liquid Fabric Detergents

Table 23 lists non-limiting examples of Fabric Detergent compositions that are evaluated for their ability to reduce fabric-friction. Fabric friction is evaluated per the Extraction Energy method outlined below. Data from these evaluations are given in Tables 24-29.

TABLE 23

| Liquid Detergent Composition | Example No. | | | | | | | |
|---|---|---|---|---|---|---|---|---|
| | 102 | 103 | 104 | 105 | 106 | 107 | 108 | 109 |
| C12-C15 alkyl polyethoxylate (1.8) sulfate[1] | 26.83 | 14.81 | — | 10.70 | 26.83 | 14.81 | — | 10.70 |
| C11.8 linear alkylbenzene sulfonc acid[2] | 4.19 | 3.53 | 10.70 | — | 4.19 | 3.53 | 10.70 | — |
| C12 alkyl dimethyl amine oxide[3] | 1.69 | 0.56 | — | — | 1.69 | 0.56 | — | — |
| C12-C14 alcohol 9 ethoxylate[4] | — | 0.78 | 10.70 | 10.70 | — | 0.78 | 10.70 | 10.70 |
| 1,2 Propane diol | — | 3.47 | 3.47 | 3.47 | — | 3.47 | 3.47 | 3.47 |
| Ethanol | — | 2.79 | 2.79 | 2.79 | — | 2.79 | 2.79 | 2.79 |
| C12-C18 Fatty Acid[5] | 1.42 | 1.48 | 1.48 | 1.48 | 1.42 | 1.48 | 1.48 | 1.48 |
| Citric acid[6] | 5.34 | 2.05 | 2.05 | 2.05 | 5.34 | 2.05 | 2.05 | 2.05 |
| Emulsion according to Example 39[7] | 20.00 | 20.00 | 20.00 | 20.00 | — | — | — | — |
| Water, perfumes, dyes, buffers, enzymes, solvents and other optional components | q.s. to 100% pH 8.0-8.2 | q.s. to 100% pH 8.0-8.2 | q.s. to 100% pH 8.0-8.2 | q.s. to 100% pH 8.0-8.2 | q.s. to 100% pH 8.0-8.2 | q.s. to 100% pH 8.0-8.2 | q.s. to 100% pH 8.0-8.2 | q.s. to 100% pH 8.0-8.2 |

[1]Available from Shell Chemicals, Houston, TX.
[2]Available from Huntsman Chemicals, Salt Lake City, UT.
[3]Available from The Procter &amble Company, Cincinnati, OH.
[4]Available from Sasol Chemicals, Johannesburg, South Africa
[5]Available from The Procter &amble Company, Cincinnati, OH.
[6]Available from Ciba Specialty Chemicals, High Point, NC
[7]Comprising organopolysiloxane conditioning polymers of Examples 9, 10, 28, 29, 30, 33, 34

TABLE 24

| Liquid Detergent Composition | Example No. | | |
|---|---|---|---|
| | 110 | 111 | 112 |
| C24 alkyl polyethoxylate (3.0) sulfate[1] | 6.8 | 6.8 | 6.8 |
| C11.8 linear alkylbenzene sulfonic acid[2] | 3.1 | 3.1 | 3.1 |
| C24 alkyl 7-ethoxylate[1] | 0.93 | 0.93 | 0.93 |
| C45 alkyl 7-ethoxylate[3] | 2.80 | 2.80 | 2.80 |
| 1,2 Propane diol | 4.58 | 4.58 | 4.58 |
| Ethanol | 0.86 | 0.86 | 0.86 |
| Di Ethylenelycol | — | — | — |
| Na Cumene Sulfonate | — | — | — |
| C12-C18 Fatty Acid | 4.1 | 4.1 | 4.1 |
| Citric acid | 3.2 | 3.2 | 3.2 |
| Protease (40.6 mg/g/) | 0.021 | 0.021 | 0.021 |
| Natalase 200L (29.26 mg/g) | 0.003 | 0.003 | 0.003 |
| Termamyl Ultra (25.1 mg/g) | 0.001 | 0.001 | 0.001 |
| Emulsion according to Example 39[4] | 15.00 | — | — |
| Emulsion according to Example 39[5] | — | 25.0 | — |
| Water, perfumes, dyes, buffers, neutralizers, stabilizers and other optional components | q.s. to 100% pH 8.0-8.2 | q.s. to 100% pH 8.0-8.2 | q.s. to 100% pH 8.0-8.2 |

[1]Available from Shell Chemicals, Houston, TX.
[2]Available from Huntsman Chemicals, Salt Lake City, UT.
[3]Available from Sasol Chemicals, Johannesburg, South Africa
[4]Comprising organopolysiloxane conditioning polymers of Examples 9, 10, 28, 29, 30, 33, 34
[5]Comprising organopolysiloxane conditioning polymer of Example 9

Mini-Washer Treatment

Euro Touch terry fabrics treated with fabric care composition of Examples 102-109 are treated in a top loader mini-washer washing machine. The water hardness is set for 6 pg and the water temperature to 90° C. during wash and 60° C. during rinse. Dry cloth fabric around 300 g are added. The 6.38 grams dose of liquid detergent formulation is added to 2 gallons of 6 GPG water (grains per gallons) and wash for 12 min. Fabrics are rinse for 2 min and tumble dried for 45 min. This procedure is repeated 3 times.

Extraction Energy Softness Test

Fabrics treated in the mini-washer are dried and equilibrated in a controlled humidity room. Fabrics are cut into circles of 4.45 in (11.5 cm) diameter. Three plates with a total weight of 3 pounds are used to push the fabric circles through a 32 mm ring. Extraction energy is measured as the fabric is pushed through the ring. Formulations without the organopolysiloxane conditioning polymer are used as controls. These controls are reflected as examples 106, 107, 108, and 109 as controls for examples 102, 103, 104, and 105 respectively. As the skilled artisan would recognize, the amount and ratio of various surfs can be varied to achieve desired results; in the particular formulations below, it should be noted that the performance of various samples varied depending upon chassis chosen; the skilled artisan will be able to utilize this information to formulate compositions having the desired performance level

TABLE 25

| Liquid Detergent | EXTRACTION ENERGY (volts) |
|---|---|
| Liquid detergent according to Example 102 comprising Organopolysiloxane conditioning polymer of Example 28 | 59.45 |
| Liquid detergent according to Example 102 comprising Organopolysiloxane conditioning polymer of Example 33 | 55.99 |
| Liquid detergent according to Example 102 comprising Organopolysiloxane conditioning polymer of Example 9 | 57.58 |
| Liquid detergent according to Example 106 | 59.95 |

TABLE 26

| Liquid Detergent | EXTRACTION ENERGY (volts) |
|---|---|
| Liquid detergent according to Example 103 comprising Organopolysiloxane conditioning polymer of Example 28 | 56.02 |
| Liquid detergent according to Example 103 comprising Organopolysiloxane conditioning polymer of Example 10 | 57.80 |
| Liquid detergent according to Example 103 comprising Organopolysiloxane conditioning polymer of Example 33 | 58.73 |
| Liquid detergent according to Example 103 comprising Organopolysiloxane conditioning polymer of Example 29 | 63.51 |
| Liquid detergent according to Example 103 comprising Organopolysiloxane conditioning polymer of Example 30 | 64.32 |
| Liquid detergent according to Example 103 comprising Organopolysiloxane conditioning polymer of Example 34 | 64.02 |
| Liquid detergent according to Example 107 | 61.80 |

TABLE 27

| Liquid Detergent | EXTRACTION ENERGY (volts) |
|---|---|
| Liquid detergent according to Example 104 comprising Organopolysiloxane conditioning polymer of Example 28 | 66.77 |
| Liquid detergent according to Example 104 comprising Organopolysiloxane conditioning polymer of Example 10 | 59.89 |
| Liquid detergent according to Example 104 comprising Organopolysiloxane conditioning polymer of Example 33 | 64.98 |
| Liquid detergent according to Example 104 comprising Organopolysiloxane conditioning polymer of Example 29 | 56.67 |
| Liquid detergent according to Example 104 comprising Organopolysiloxane conditioning polymer of Example 30 | 59.78 |
| Liquid detergent according to Example 104 comprising Organopolysiloxane conditioning polymer of Example 34 | 59.78 |
| Liquid detergent according to Example 108 | 66.77 |

TABLE 28

| Liquid Detergent | EXTRACTION ENERGY (volts) |
|---|---|
| Liquid detergent according to Example 105 comprising Organopolysiloxane conditioning polymer of Example 10 | 54.66 |
| Liquid detergent according to Example 105 comprising Organopolysiloxane conditioning polymer of Example 33 | 60.40 |
| Liquid detergent according to Example 105 comprising Organopolysiloxane conditioning polymer of Example 29 | 57.57 |
| Liquid detergent according to Example 105 comprising Organopolysiloxane conditioning polymer of Example 30 | 59.57 |
| Liquid detergent according to Example 105 comprising Organopolysiloxane conditioning polymer of Example 34 | 57.22 |
| Liquid detergent according to Example 109 | 61.82 |

Table 24 lists non-limiting examples of Fabric Detergent compositions that are evaluated for their ability to reduce fabric-friction. Fabric friction is evaluated per the Twing-Albert method outlined below. Data from these evaluations are given in Table 29.

Duet Washer Treatment

Fabrics treated with Fabric care composition of Examples 110-112 are treated in a front-loader (Whirlpool Duet) washing machine. The water hardness is set for 6 gpg and the water temperature to 90° C. during wash and 60° C. during rinse. Dry cloth fabric around 3628.74 grams-3855.54 grams are added to the drum and the Duet washer is set to "Normal". The 66.5 grams liquid detergent formulation is shaken with 59 mL of water, then dosed into the dispensing drawer of the front loader-type washing machine and rinsed with water until the drawer is empty. The total "Normal" cycle lasts for 50 minutes and is divided between two fill-tumble-drain & spin cycles followed by a rinse fill and alternating tumble and spin cycles. The fabrics are transferred to a dryer set to high and tumbled for 40 minutes. The procedure is repeated three times.

Twin Albert Fabric Friction Test

A Thwing-Albert FP2250 Friction/Peel Tester with a 2 kilogram force load cell is used to measure fabric to fabric friction. (Thwing Albert Instrument Company, West Berlin, N.J.). The sled is a clamping style sled with a 6.4 by 6.4 cm footprint and weighs 200 (Thwing Albert Model Number 00225-218). The distance between the load cell to the sled is set at 10.2 cm. The crosshead arm height to the sample stage is adjusted to 25 mm (measured from the bottom of the cross arm to the top of the stage) to ensure that the sled remains parallel to and in contact with the fabric during the measurement. The 11.4 cm×6.4 cm cut fabric piece is attached to the clamping sled so that the face of the fabric on the sled is pulled across the face of the fabric on the sample plate. The sled is placed on the fabric and attached to the load cell. The crosshead is moved until the load cell registers between ~1.0-2.0 gf. Then, it is moved back until the load reads 0.0 gf. At this point the measurement is made and the Kinetic Coefficient of Friction (kCOF) recorded. For each treatment, at least ten replicate fabrics are measured. The example composition 112 was used as the experimental control for examples 110 and 111.

TABLE 29

| Liquid Detergent | CoF (gF) |
|---|---|
| Liquid detergent according to Example 110 comprising Organopolysiloxane conditioning polymer of Example 28 | 1.46 |
| Liquid detergent according to Example 111 comprising Organopolysiloxane conditioning polymer of Example 28 | 1.10 |
| Liquid detergent according to Example 110 comprising Organopolysiloxane conditioning polymer of Example 30 | 1.47 |
| Liquid detergent according to Example 110 comprising Organopolysiloxane conditioning polymer of Example 34 | 1.37 |
| Liquid detergent according to Example 110 comprising Organopolysiloxane conditioning polymer of Example 29 | 1.64 |
| Liquid detergent according to Example 110 comprising Organopolysiloxane conditioning polymer of Example 10 | 1.62 |
| Liquid detergent according to Example 110 comprising Organopolysiloxane conditioning polymer of Example 33 | 1.66 |
| Liquid detergent according to Example 112 | 1.67 |

Fabric Enhancer Friction Results

Table 30 lists non-limiting examples of Fabric Enhancer compositions that are evaluated for their ability to reduce fabric-friction. Fabric friction is evaluated per the Extraction Energy method outlined below. Data from these evaluations are given in Table 31.

TABLE 30

| EXAMPLE COMPOSITION | 113 |
| --- | --- |
| Fabric Softener Active[1] | 11.0 |
| Fabric Softener Active[2] | — |
| Cationic Starch[3] | — |
| Polyethylene imine[4] | — |
| Quaternized polyacrylamide[5] | 0.2 |
| Calcium chloride | 0.15 |
| Ammonium chloride | 0.1 |
| Suds Suppressor[6] | — |
| Emulsion according to Examples 39[7] | 15.0 |
| Perfume | 2.0 |
| Perfume microcapsule[8] | 0.75 |
| Water, suds suppressor, stabilizers, pH control agents, buffers, dyes & other optional ingredients | q.s. to 100% pH = 3.0 |

[1]N,N di(tallowoyloxyethyl) - N,N dimethylammonium chloride available from Evonik Corporation, Hopewell, VA.
[2]Reaction product of fatty acid with Methyldiethanolamine, quaternized with Methylchloride, resulting in a 2.5:1 molar mixture of N,N-di(tallowoyloxyethyl) N,N-dimethylammonium chloride and N-(tallowoyloxyethyl) N-hydroxyethyl N,N-dimethylammonium chloride available from Evonik Corporation, Hopewell, VA.
[3]Cationic starch based on common maize starch or potato starch, containing 25% to 95% amylose and a degree of substitution of from 0.02 to 0.09, and having a viscosity measured as Water Fluidity having a value from 50 to 84. Available from National Starch, Bridgewater, NJ
[4]Available from Nippon Shokubai Company, Tokyo, Japan under the trade name Epomin 1050.
[5]Cationic polyacrylamide polymer such as a copolymer of acrylamide/[2-(acryloylamino) ethyl]trimethylammonium chloride (quaternized dimethyl aminoethyl acrylate) available from BASF, AG, Ludwigshafen under the trade name Sedipur 544.
[6]SILFOAM® SE90 available from Wacker AG of Munich, ermany
[7]Comprising organopolysiloxane conditioning polymer of Example 28
[8]Available from Appleton Paper of Appleton, WI Mini-Washer Treatment Test A mini-washer machine is used to treat around 300 g Euro Touch terry fabrics with 5.8 g of Tide Free & Gentle added to 2 gal of 6 GPG water. The water hardness is set for 6 pg and the water temperature to 90° C. during wash and 60° C. during rinse. During the rinse 2.4 g dose of fabric enhancer of Examples 113 is added. A clear rinse using 6GPG water is used as a control in the test.

Phabrometer Softness Test

Fabrics are dry and equilibrated in a controlled humidity room. Fabrics are cut into circles of 4.45 in (11.5 cm) diameter. Three plates with a total weight of 3 pounds are used to push the fabric circles through a 32 mm ring. Extraction energy is measured as the fabric is pushed through the ring. A water-only evaluation is used as the control.

TABLE 31

| MATERIAL | EXTRACTION ENERGY (volts) |
| --- | --- |
| 6 GPG Water | 61.04 |
| Composition according to Example 113 Comprising organopolysiloxane conditioning polymer of Example 28 | 47.43 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising an adjunct and an organopolysiloxane conditioning agent having the formula:

$$M_w D_x T_y Q_z$$

wherein:
M=[SiR$_1$R$_2$G$_1$O$_{1/2}$], [SiR$_1$G$_1$G$_2$O$_{1/2}$], [SiR$_1$G$_1$G$_2$G$_3$O$_{1/2}$], or combinations thereof;
D=[SiR$_1$R$_2$O$_{2/2}$], [SiG$_1$G$_2$O$_{2/2}$], [SiG$_1$G$_2$O$_{2/2}$] or combinations thereof;
T=[SiR$_1$O$_{3/2}$],[SiG$_1$O$_{3/2}$] or combinations thereof;
Q=[SiO$_{4/2}$];
w=is an integer from 2 to (2+y+2z);
x=is an integer from 5 to 15,000;
y=is an integer from 0 to 98;
z=is an integer from 0 to 98;
R$_1$, R$_2$, and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$, or G$_3$; and
G$_1$, G$_2$, and G$_3$ are each independently selected from the formula:

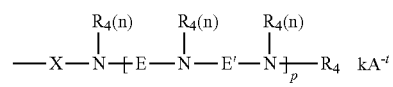

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O;
N=a nitrogen atom;
each R$_4$ comprises identical or different monovalent radicals independently selected from the group consisting of C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;

E comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

p is an integer independently selected from 1 to 50;
n is an integer independently selected from 1 or 2;
wherein at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$, or $G_3$; where t is an integer independently selected from 1, 2, or 3; and $k \leq (p^* 2/t) + 1$; such that the total number of cationic charges balances the total number of anionic charges in the organopolysiloxane molecule;
wherein at least one E does not comprise an ethylene moiety; and
wherein at least one E or E' are independently selected from the group consisting of:

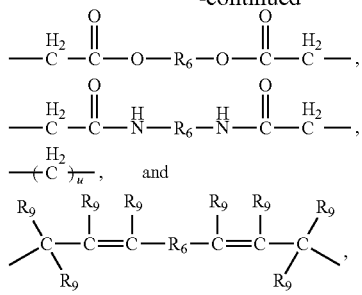

wherein:
each $R_6$ comprises a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

each $R_9$ comprises an identical or different monovalent radical independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

2. A composition according to claim 1, wherein each E comprises a divalent radical selected from the group consisting of $C_3$-$C_{32}$ alkylene, $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O; and wherein E' comprises a divalent radical selected from the group consisting of $C_3$-$C_{32}$ alkylene, $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O.

3. A consumer product composition comprising an adjunct and an organopolysiloxane conditioning agent having the formula:

$$M_w D_x$$

where:
$M = [SiR_1R_2G_1O_{1/2}]$, $[SiR_1G_1G_2O_{1/2}]$, $[SiG_1G_2G_3O_{1/2}]$, or combinations thereof;
$D = [SiR_1R_2O_{2/2}]$;
w = is 2;
x = is an integer from 5 to 15,000;
$R_1$, $R_2$, and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;

at least one of M or D incorporates at least one moiety $G_1$, $G_2$, or $G_3$, and $G_1$, $G_2$, and $G_3$ are each independently selected from the formula:

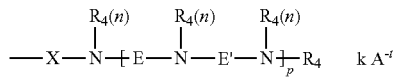

wherein:

X comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O;

N=a nitrogen atom;

each $R_4$ comprises identical or different monovalent radicals independently selected from the group consisting of $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;

E comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O;

E' comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O;

p is an integer independently selected from 1 to 50;

n is an integer independently selected from 1 or 2; and wherein at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$, or $G_3$, where t is an integer independently selected from 1, 2, or 3; and k≤(p*2/t)+1; such that the total number of cationic charges balances the total number of anionic charges in the organopolysiloxane molecule;

wherein at least one E does not comprise an ethylene moiety; and wherein at least one E or E' are independently selected from the group consisting of:

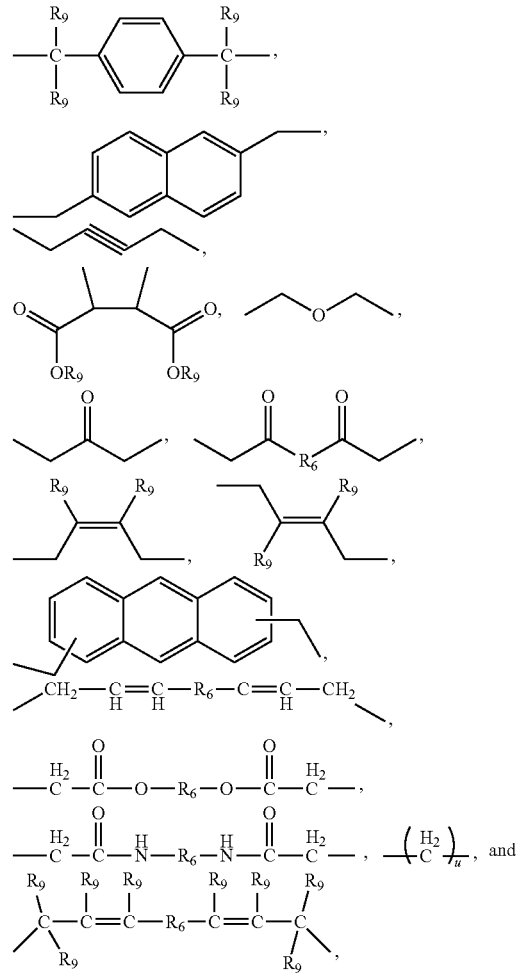

wherein:

each $R_6$ comprises a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

each $R_9$ comprises an identical or different monovalent radical independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

4. A composition according to claim 3, wherein each E comprises a divalent radical selected from the group consisting of $C_3$-$C_{32}$ alkylene, $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O; and wherein E' comprises a divalent radical selected from the group consisting of $C_3$-$C_{32}$ alkylene, $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O.

5. The composition of claim 1, wherein the adjunct is selected from the group consisting of bleach, bleach activators, surfactants, builders, chelating agents, dye transfer inhibiting agents, dispersants, enzymes, enzyme stabilizers, catalytic metal complexes, polymers, polymeric dispersing agents, clay and soil removal/anti-redeposition agents, brighteners, fluorescent whitening agents, suds suppressors, dyes, perfumes, perfume delivery systems, structure elasticizing agents, fabric softeners, carriers, hydrotropes, solvents, processing aids, conditioning agents, perfume microcapsules, emollients, fatty alcohols, delivery enhancing agents, pigments, high melting point fatty compounds, cationic polymers, anti-dandruff actives, humectant, skin care actives, silicone, silicone resin, silicone waxes, a material comprising a hydrocarbon wax, a hydrocarbon liquid, a sugar polyester, a sugar polyether, hydrocarbon waxes, polyolefin waxes, polyethylene and polypropylene waxes, modified polyethylene and polypropylene waxes, polyisobutene, substituted polyisobutene, isobutene, essential oils, lipids, skin coolants, vitamins, sunscreens, antioxidants, glycerine, catalysts, silicon dioxide particles, malodor reducing agents, odor-controlling materials, antistatic agents, softening agents, insect and moth repelling agents, colorants, antioxidants, bodying agents, drape and form control agents, smoothness agents, wrinkle control agents, sanitization agents, antibacterial disinfecting agent, germ control agents, mold and mildew control agents, antiviral agents, drying agents, stain resistance agents, soil release agents, fabric refreshing agents and freshness extending agents, dye fixatives, dye transfer inhibitors, color maintenance agents, optical brighteners, color restoration/rejuvenation agents, anti-fading agents, whiteness enhancers, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, natural agents, antiperspirant actives, dyes, emollients, fatty alcohols, gel networks, and mixtures thereof.

6. The composition of claim 1, wherein the adjunct comprises a material selected from the group consisting of a silicone, a silicone resin, a silicone wax, or combinations thereof.

7. The composition of claim 1, wherein the adjunct comprises a material selected from the group consisting of anionic surfactant, cationic surfactant, nonionic surfactant, zwitterionic surfactant, amphoteric surfactant, and combinations thereof.

8. The composition of claim 1, wherein said composition is a fabric care composition comprising an adjunct selected from the group consisting of:

a. an anionic surfactant selected from the group consisting of a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, alkyls, alkyl ether sulfates, succinnates, olefin sulfonates, beta-alkyloxy alkane sulfonates and mixtures thereof, b. a cationic surfactant selected from the group consisting of mono-long alkyl quaternized ammonium salt cationic surfactants, mono-alkyl amines, di-alkyl chain cationic surfactants, and mixtures thereof, c. a conditioning active selected from the group consisting of silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein, and d. mixtures thereof.

9. The composition of claim 8 wherein said adjunct further comprises a stabilizer.

10. The composition of claim 1, wherein the composition is a personal care composition comprising an adjunct selected from the groups consisting of:

a. an anionic surfactant selected from the group consisting of a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, alkyls, alkyl ether sulfates, succinnates, olefin sulfonates, beta-alkyloxy alkane sulfonates and mixtures thereof, b. a cationic surfactant selected from the group consisting of mono-long alkyl quaternized ammonium salt cationic surfactants, mono-alkyl amines, di-alkyl chain cationic surfactants, and mixtures thereof, c. a conditioning active selected from the group consisting of silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein, and d. mixtures thereof.

11. The composition of claim 10, wherein said adjunct comprises a cationic surfactant selected from the group consisting of mono-long alkyl quaternized ammonium salt cationic surfactants, mono-alkyl amines, di-alkyl chain cationic surfactants, and mixtures thereof.

12. The composition of claim 11, wherein said adjunct further comprises a high melting point fatty compound selected from the group consisting of fatty alcohols, fatty acids, fatty alcohol derivatives, fatty acid derivatives, and mixtures thereof.

13. The composition of claim 1, wherein each p is an integer selected from about 1 to about 40.

14. The composition of claim 1, wherein the molecular weight of said organopolysiloxane is from about 10,000 Daltons to about 1,000,000 Daltons; from about 20,000 Daltons to about 500,000 Daltons; or from about 25,000 Daltons to about 50,000 Daltons.

15. The composition of claim 1, wherein said organopolysiloxane has a charge density of from 0.05 meq/g to 12 meq/g; or from 0.1 meq/g to 10 meq/g; or from 0.1 to 5 meq/g.

16. A method of treating a substrate, comprising contacting said substrate with the composition of claim 1.

* * * * *